(12) United States Patent
Meeker et al.

(10) Patent No.: US 12,708,785 B2
(45) Date of Patent: Aug. 18, 2026

(54) ELECTRODE CONTAINMENT STRUCTURES IN A WEARABLE MEDICAL DEVICE

(71) Applicant: West Affum Holdings Designated Activity Company, Dublin (IE)

(72) Inventors: Dallas E. Meeker, Kirkland, WA (US); Daniel R. Piha, Mercer Island, WA (US); Joseph L. Sullivan, Kirkland, WA (US); Robert R. Buchanan, Bothell, WA (US); Philip D. Foshee, Jr., Woodinville, WA (US)

(73) Assignee: West Affum Holdings DAC, Dublin (IE)

( * ) Notice: Subject to any disclaimer, the term of this patent is extended or adjusted under 35 U.S.C. 154(b) by 293 days.

(21) Appl. No.: 18/490,748

(22) Filed: Oct. 19, 2023

(65) Prior Publication Data

US 2024/0157160 A1 May 16, 2024

Related U.S. Application Data

(60) Provisional application No. 63/420,397, filed on Oct. 28, 2022.

(51) Int. Cl.
*A61N 1/04* (2006.01)
*A61B 5/256* (2021.01)
(Continued)

(52) U.S. Cl.
CPC ............ *A61N 1/3904* (2017.08); *A61B 5/256* (2021.01); *A61B 5/282* (2021.01); *A61B 5/332* (2021.01); *A61N 1/046* (2013.01); *A61N 1/0484* (2013.01)

(58) Field of Classification Search
CPC .... A61N 1/3904; A61N 1/046; A61N 1/0484; A61B 5/256
See application file for complete search history.

(56) References Cited

U.S. PATENT DOCUMENTS 3,724,355 A 4/1973 Busch et al.
3,724,455 A 4/1973 Unger
(Continued)

FOREIGN PATENT DOCUMENTS

DE 102005060985 A2 6/2007
EP 2305110 A1 4/2011
(Continued)

OTHER PUBLICATIONS

Heartstart MRx and XL AED Algorithm-Application Note, Jul. 2001, Edition 2 Philips Healthcare, USA.
(Continued)

*Primary Examiner* — Eric D. Bertram
(74) *Attorney, Agent, or Firm* — Lisa Benado; Propel IP Law, PLLC

(57) ABSTRACT

A wearable article is provided as a wearable component of a medical device configured with elements to accommodate electrode pads in a manner that offers flexibility, cushion, and temperature regulation for comfort of a patient, as well as facilitating distribution of pressure on the electrode pads against the body of the patient. A containment portion of the wearable article houses the electrode pad and a spacer structure. The spacer structure is flexible to move as the body of the patient moves and yet provides a level of stiffness for pressure on the underlying electrode. Numerous springy elements dispersed in the spacer structure provide a thickness and open space for air circulation through the spacer structure, resulting in temperature regulation of the wearable article.

16 Claims, 10 Drawing Sheets

(51) Int. Cl.

| | |
|---|---|
| *A61B 5/282* | (2021.01) |
| *A61B 5/332* | (2021.01) |
| *A61N 1/39* | (2006.01) |

(56) References Cited

U.S. PATENT DOCUMENTS 4,583,524 A 4/1986 Hutchins
4,619,265 A 10/1986 Morgan et al.
4,666,432 A 5/1987 McNeish et al.
4,698,848 A 10/1987 Buckley
4,928,690 A 5/1990 Heilman et al.
4,955,381 A 9/1990 Way et al.
5,078,134 A 1/1992 Heilman et al.
5,228,449 A 7/1993 Christ et al.
5,348,008 A 9/1994 Bornn et al.
5,353,793 A 10/1994 Bornn
RE34,800 E 11/1994 Hutchins
5,394,892 A 3/1995 Kenny et al.
5,405,362 A 4/1995 Kramer et al.
5,429,593 A 7/1995 Matory
5,474,574 A 12/1995 Payne et al.
5,618,208 A 4/1997 Crouse et al.
5,662,690 A 9/1997 Cole et al.
5,708,978 A 1/1998 Johnsrud
5,741,306 A 4/1998 Glegyak et al.
5,782,878 A 7/1998 Morgan et al.
5,792,204 A 8/1998 Snell
5,902,249 A 5/1999 Lyster
5,913,685 A 6/1999 Hutchins
5,944,669 A 8/1999 Kaib
6,047,203 A 4/2000 Sackner et al.
6,065,154 A * 5/2000 Hulings ................. A61N 1/321 600/389
6,108,197 A 8/2000 Janik
6,148,233 A 11/2000 Owen et al.
6,201,992 B1 3/2001 Freeman
6,263,238 B1 7/2001 Brewer et al.
6,280,461 B1 8/2001 Glegyak et al.
6,287,328 B1 9/2001 Snyder et al.
6,304,780 B1 10/2001 Owen et al.
6,319,011 B1 11/2001 Motti et al.
6,334,070 B1 12/2001 Nova et al.
6,356,785 B1 3/2002 Snyder et al.
6,427,083 B1 7/2002 Owen et al.
6,437,083 B1 8/2002 Brack et al.
6,450,942 B1 9/2002 Lapanashvili et al.
6,529,875 B1 3/2003 Nakajima et al.
6,546,285 B1 4/2003 Owen et al.
6,671,545 B2 12/2003 Fincke
6,681,003 B2 1/2004 Linder et al.
6,762,917 B1 7/2004 Verbiest et al.
7,065,401 B2 6/2006 Worden
7,099,715 B2 8/2006 Korzinov
7,212,850 B2 5/2007 Prystowsky
7,559,902 B2 7/2009 Ting et al.
7,587,237 B2 9/2009 Korzinov
7,753,759 B2 7/2010 Pintor et al.
7,865,238 B2 1/2011 Brink
7,870,761 B2 1/2011 Valentine et al.
7,907,996 B2 3/2011 Prystowsky
7,941,207 B2 5/2011 Korzinov
7,974,689 B2 7/2011 Volpe et al.
8,135,462 B2 3/2012 Owen et al.
8,140,154 B2 3/2012 Donnelly et al.
8,369,944 B2 2/2013 Macho et al.
8,527,028 B2 9/2013 Kurzweil et al.
8,548,557 B2 10/2013 Garstka et al.
8,560,044 B2 10/2013 Kurzweil et al.
8,615,295 B2 12/2013 Savage et al.
8,644,925 B2 2/2014 Volpe et al.
8,676,313 B2 3/2014 Volpe et al.
8,706,255 B2 4/2014 Phillips et al.
8,742,349 B2 6/2014 Urbon et al.
8,897,860 B2 11/2014 Volpe et al.
8,904,214 B2 12/2014 Volpe et al.
8,965,500 B2 2/2015 Macho et al.
9,008,801 B2 4/2015 Kaib et al.
9,084,583 B2 7/2015 Mazar et al.
9,089,685 B2 7/2015 Sullivan et al.
9,119,547 B2 9/2015 Cazares et al.
9,131,901 B2 9/2015 Volpe et al.
9,132,267 B2 9/2015 Kaib
9,265,432 B2 2/2016 Warren et al.
9,345,898 B2 5/2016 Piha et al.
9,408,548 B2 8/2016 Volpe et al.
9,445,719 B2 9/2016 Libbus et al.
9,454,219 B2 9/2016 Volpe et al.
9,579,020 B2 2/2017 Libbus et al.
9,592,403 B2 3/2017 Sullivan
9,598,799 B2 3/2017 Shoshani et al.
9,675,804 B2 6/2017 Whiting et al.
9,724,008 B2 8/2017 Sullivan et al.
9,878,171 B2 1/2018 Kaib
9,895,105 B2 2/2018 Romem
9,901,741 B2 2/2018 Chapman et al.
RE46,926 E 7/2018 Bly et al.
10,076,656 B2 9/2018 Dar et al.
10,192,387 B2 1/2019 Brinig et al.
10,307,133 B2 6/2019 Kaib
10,463,867 B2 11/2019 Kaib et al.
10,589,110 B2 3/2020 Oskin et al.
10,599,814 B2 3/2020 Landrum et al.
11,857,329 B2 * 1/2024 Gabrin ................... A61B 5/361
12,115,366 B2 10/2024 Gustavson et al.
2002/0181680 A1 12/2002 Linder et al.
2003/0158593 A1 8/2003 Heilman et al.
2005/0107833 A1 5/2005 Freeman et al.
2005/0107834 A1 5/2005 Freeman et al.
2006/0173499 A1 8/2006 Hampton et al.
2008/0312709 A1 12/2008 Volpe et al.
2009/0005827 A1 1/2009 Weintraub et al.
2010/0007413 A1 1/2010 Herleikson et al.
2010/0298899 A1 11/2010 Donnelly et al.
2011/0022105 A9 1/2011 Owen et al.
2011/0288604 A1 11/2011 Kaib et al.
2011/0288605 A1 11/2011 Kaib et al.
2012/0112903 A1 5/2012 Kaib et al.
2012/0144551 A1 6/2012 Guldalian
2012/0150008 A1 6/2012 Kaib et al.
2012/0158075 A1 6/2012 Kaib et al.
2012/0191476 A1 7/2012 Reid et al.
2012/0265265 A1 10/2012 Razavi et al.
2012/0283794 A1 11/2012 Kaib et al.
2012/0293323 A1 11/2012 Kaib et al.
2012/0302860 A1 11/2012 Volpe et al.
2012/0310315 A1 12/2012 Savage et al.
2013/0085538 A1 4/2013 Volpe et al.
2013/0144355 A1 6/2013 Macho et al.
2013/0231711 A1 9/2013 Kaib
2013/0245388 A1 9/2013 Rafferty et al.
2013/0274565 A1 10/2013 Langer et al.
2013/0317852 A1 11/2013 Worrell et al.
2013/0325078 A1 12/2013 Whiting et al.
2014/0012144 A1 1/2014 Crone
2014/0025131 A1 1/2014 Sullivan et al.
2014/0046391 A1 2/2014 Cowan et al.
2014/0070957 A1 3/2014 Longinotti-Buitoni et al.
2014/0163663 A1 6/2014 Poddar et al.
2014/0324112 A1 10/2014 Macho et al.
2014/0378812 A1 12/2014 Saroka et al.
2015/0039053 A1 2/2015 Kaib et al.
2015/0161554 A1 6/2015 Sweeney et al.
2015/0297135 A1 10/2015 Shoshani et al.
2015/0328472 A1 11/2015 Sullivan et al.
2016/0004831 A1 1/2016 Carlson et al.
2016/0076175 A1 3/2016 Rock et al.
2016/0076176 A1 3/2016 Rock et al.
2016/0082277 A1 3/2016 Foshee, Jr. et al.
2016/0113581 A1 4/2016 Amir et al.
2016/0256104 A1 9/2016 Romem et al.
2016/0283900 A1 9/2016 Johnson et al.
2017/0014073 A1 1/2017 Shoshani et al.
2017/0027469 A1 2/2017 Amir et al.
2017/0036066 A1 2/2017 Chahine

(56) References Cited

U.S. PATENT DOCUMENTS

| | | | | |
|---|---|---|---|---|
| 2017/0040758 | A1 | 2/2017 | Amir et al. | |
| 2017/0162840 | A1 | 6/2017 | Pendry | |
| 2017/0319862 | A1 | 11/2017 | Foshee, Jr. et al. | |
| 2017/0367591 | A1 | 12/2017 | Jorgensen | |
| 2018/0001101 | A1* | 1/2018 | Hulings | A61N 1/3968 |
| 2018/0116537 | A1 | 5/2018 | Sullivan et al. | |
| 2018/0117299 | A1 | 5/2018 | Gustavson et al. | |
| 2018/0184933 | A1 | 7/2018 | Sullivan et al. | |
| 2018/0185662 | A1 | 7/2018 | Foshee, Jr. et al. | |
| 2018/0221648 | A1* | 8/2018 | Gustavson | A61N 1/0484 |
| 2018/0243578 | A1 | 8/2018 | Volosin | |
| 2018/0272147 | A1* | 9/2018 | Freeman | G16H 50/30 |
| 2018/0361165 | A1 | 12/2018 | Jaax et al. | |
| 2019/0030352 | A1 | 1/2019 | Sullivan et al. | |
| 2019/0076666 | A1 | 3/2019 | Medema | |
| 2019/0116896 | A1 | 4/2019 | Armour et al. | |
| 2019/0321650 | A1 | 10/2019 | Raymond et al. | |
| 2022/0104566 | A1* | 4/2022 | Skalos | A61N 1/046 |
| 2022/0249024 | A1* | 8/2022 | Hulings | A61N 1/3925 |
| 2022/0370788 | A1* | 11/2022 | Freeman | A61B 5/282 |

FOREIGN PATENT DOCUMENTS

| | | | |
|---|---|---|---|
| JP | 2005507747 | A | 3/2005 |
| JP | 2014500099 | A | 1/2014 |
| JP | 2014526282 | A2 | 10/2014 |
| WO | 9839061 | A1 | 9/1998 |
| WO | 2011/146448 | A1 | 11/2011 |
| WO | 2012/064604 | A1 | 5/2012 |
| WO | 2012/151160 | A1 | 11/2012 |
| WO | 2015/056262 | A1 | 4/2015 |
| WO | 2023107404 | A2 | 6/2023 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

Zoll, LifeVest, Proven protection from Sudden Cardiac Death, issued Mar. 27, 2018, 4 pages. Pittsburgh PA, USA.

International Search Report and Written Opinion for PCT Application No. PCT/US2015/051726, dated May 20, 2016, European Patent Office, Rijswijk, 11 pages.

Screen capture from Bowi-Style website, Oct. 18, 20233—D Spacer Fabric [online], Retrieved from Internet https://www.bowistyl.pl/products/3d-spacer-fabric/3d-spacer-fabric/.

* cited by examiner

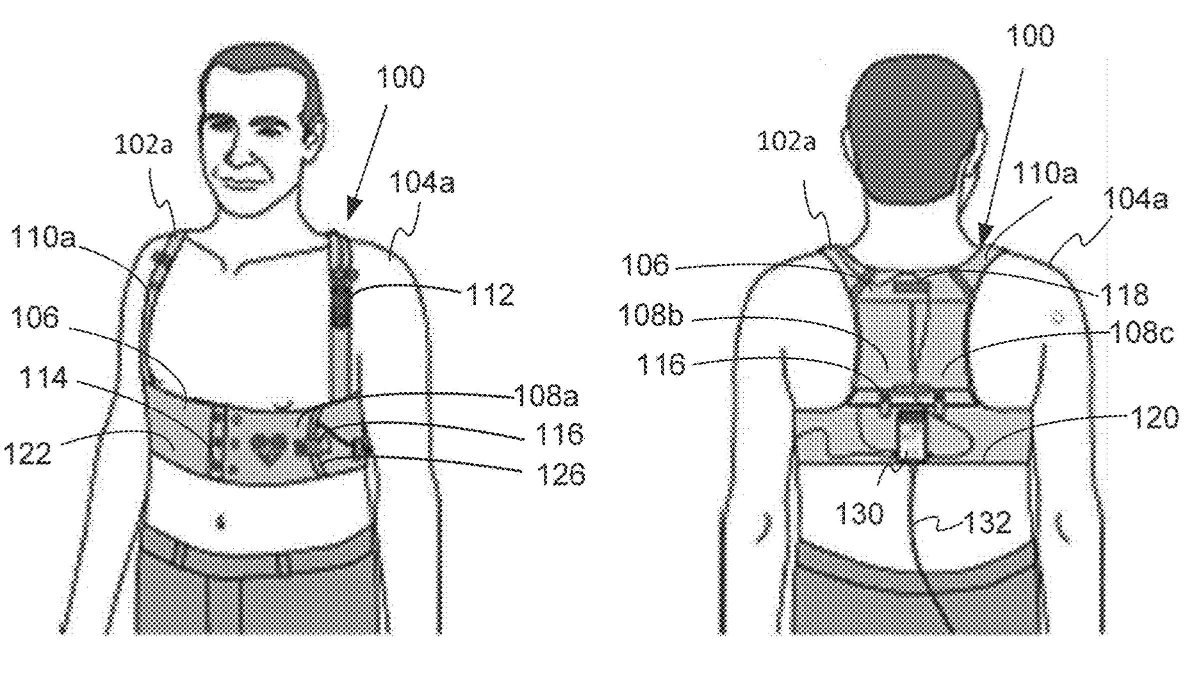
FIG. 1A
FIG. 1B
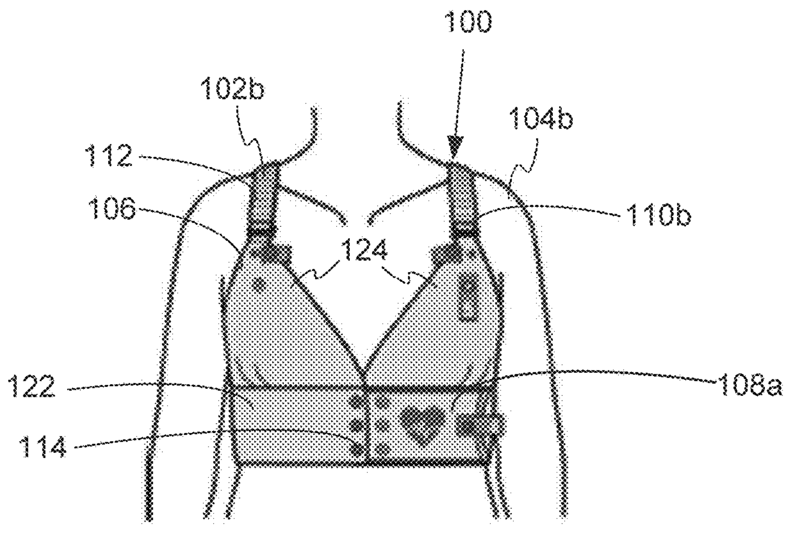
FIG. 1C

ELECTRODE CONTAINMENT STRUCTURES IN A WEARABLE MEDICAL DEVICE

CROSS REFERENCES TO RELATED APPLICATIONS

This application claims the benefit of the filing date of U.S. Provisional Patent Application No. 63/420,397 filed Oct. 28, 2022, the disclosure of which is hereby incorporated herein by reference for all purposes.

FIELD OF THE INVENTION

The present disclosure generally relates to cardiac medical care using a wearable medical device.

BACKGROUND

Various medical devices can be worn by a patient during treatment and/or monitor of patient health. For example, wearable devices used in cardiac care can incorporate electrocardiogram (ECG) electrodes that electrically interact with the patient during day-to-day activities. Some ECGs detect electrical impulses of the heart that are translated and recorded as a wavy graph line. Certain wearable devices use defibrillator electrodes to transmit an appropriate shock energy to the patient. To function properly, electrodes should maintain close contact with the body of the patient during treatment and monitoring.

Wearable medical devices need to ensure adequate contact yet provide a level of comfort for the well-being of the patient. Wearables that accommodate the needs of the patient encourage patient compliance with wearing requirements and facilitate proper function. Wearable medical devices that are uncomfortable, for example, which trap heat or are stiff and hinder body movement, can result in improper use of the wearable device.

SUMMARY

Elements of a wearable article are provided to house an electrode for cardiac patient care. The present features of the wearable article are configured to offer a balance between force exerted on an electrode for firm contact with a patient and ease of use for the patient. A spacer structure is positioned at a containment portion of the wearable that holds the electrode. The spacer structure allows for cushion and temperature regulation for the patient. The spacer structure can also enable pressure to be distributed across the electrode, for example from an outer side of the wearable article through the spacer structure, or by confining a pressure built up from within the containment portion. Pressure exerted on an electrode pad that holds the electrode may urge the electrode against the body of the patient.

A wearable article for cardiac medical care of a patient is provided having a containment portion and one or more flexible support materials configured to retain the containment portion. The containment portion may be sized to house at least one electrode pad when the electrode pad is inserted into the containment portion. The containment portion has an inner material configured to contact the electrode pad. A spacer structure is positioned in the containment portion to provide a cushioned area for pressure on the at least one electrode pad. The spacer structure may include a top permeable layer positioned toward the electrode pad, and a bottom permeable layer that is opposite of the top permeable layer. A compressible middle layer having a plurality of springy elements is dispersed between the top permeable layer and the bottom permeable layer for airflow through the spacer structure.

In some implementations of the spacer structure that is provided in the wearable article has a top permeable layer and/or the bottom permeable layer that includes a knitted mesh. The plurality of springy elements may also include a plurality of knitted filaments extending between the top permeable layer and the bottom permeable layer. The spacer structure may be coupled to an outer layer of the containment portion to resist pressure increase within the containment portion, thereby enabling pressure to be exerted onto the at least one electrode pad in a direction toward the patient.

In some implementations, pressure may be increased within the containment portion, such inside one or more resilient fluid pack, by gas injected into the containment portion and into the fluid pack(s) to release a fluid at the inner material of the containment portion and onto the patient. Further, the top permeable layer, the bottom permeable layer and the compressible middle layer can include material resistant to moisture absorption. The containment portion may also include a stiffened outer layer proximal to the spacer structure, wherein the stiffened outer layer has greater rigidity than the one or more flexible support material. In some implementations, the spacer structure can have a thickness between about 2 mm to 15 mm. The spacer structure may have a density of about 450 g/m$^2$. The inner material of the containment portion may include an electrically conducting lining.

In some aspects of the present wearable medical device that employs a wearable article as described herein, components are provided for cardiac defibrillation of a patient. For example, a defibrillator electrode pad is provided for electrical shock treatment to the patient upon activation. The wearable article includes one or more flexible support material configured to hold a containment portion on the patient. The containment portion may be sized to house the defibrillator electrode pad and comprise a spacer structure positioned to provide a cushioned area for pressure on the defibrillator electrode pad during the electrical shock treatment. Such spacer structure includes a top permeable layer positioned toward the defibrillator electrode pad, a bottom permeable layer opposite of the top permeable layer, and a compressible middle layer having a plurality of springy elements dispersed between the top permeable layer and the bottom permeable layer for airflow through the spacer structure. The medical device may also include one or more processors to determine the electrical shock treatment and based on the determination, to activate the defibrillator electrode pad.

In some implementations of the wearable medical device for cardiac defibrillation, the spacer structure employed in the wearable article has a top permeable layer and/or the bottom permeable layer that includes a knitted mesh and the plurality of springy elements include a plurality of knitted filaments extending between the top permeable layer and the bottom permeable layer. The containment portion can include one or more fluid packs coupled to the defibrillator electrode pad to release fluid upon injection of a gas into the containment portion. In such constructions, the spacer structure, coupled to an outer layer, may be configured to resist pressure increase in the containment portion, thereby enabling pressure to be exerted onto the defibrillator electrode pad in a direction toward the patient. Furthermore, the outer layer may be a stiffened material having a greater rigidity than a rigidity of the one or more flexible support material. The containment portion may also comprise an electrically conducting lining configured to contact the defibrillator electrode pad proximal to the patient. In the medical device, one or more monitoring electrodes may be employed to detect electrical signals for generating electrocardiogram (ECG) data, wherein the one or more processors determine the electrical shock treatment based, at least in part, on the ECG data.

In some implementations, a method is provided for providing cardiac defibrillation to a patient using a wearable article. In the method, a defibrillator electrode pad may be inserted into a containment portion of a wearable article. The containment portion may comprise an attached spacer structure positioned to provide a cushioned area for pressure on the defibrillator electrode pad, The spacer structure may be configured with a top permeable layer positioned toward the defibrillator electrode pad and a bottom permeable layer opposite of the top permeable layer. The spacer structure also has a compressible middle layer having a plurality of springy elements dispersed between the top permeable layer and the bottom permeable layer for airflow through the spacer structure. Such spacer structure may include the top permeable layer and/or the bottom permeable layer of a knitted mesh and the plurality of springy elements may include a plurality of knitted filaments extending between the top permeable layer and the bottom permeable layer.

The method additionally includes an activation step to initiate a treatment session for the patient. In response to activating the treatment session, a gas is injected into one or more fluid packs, thereby causing the spacer structure to compress and change shape in resistance to a pressure increase within the containment portion, and enabling fluid to be released from the one or more fluid packs at the defibrillator electrode pad onto the patient. Furthermore, the defibrillator electrode pad is activated to provide an electrical shock treatment to the patient.

In some implementations of the method described, the gas is injected as the fluid is released at the electrode to at least substantially maintain pressure in the containment portion during the electrical shock treatment. Furthermore, upon completion of the electrical shock treatment, the gas may cease to be further injected into the fluid pack(s), thereby decreasing pressure in the containment portion and causing the spacer structure to decompress into an original shape. Thereafter, the electrode pad may be removed from the containment portion; and the wearable article washed with the attached spacer structure for future use by the patient.

This summary is not intended to identify key features of the claimed subject matter, nor is it intended to be used as an aid in determining the scope of the claimed subject matter.

BRIEF DESCRIPTION OF THE DRAWINGS

Various implementations in accordance with the present disclosure will be described with reference to the drawings.

FIGS. 1A-1C are diagrams illustrating examples of outer sides of wearable medical articles worn by patients, in which FIG. 1A shows a front view of a first vest style wearable designed for a first body type, FIG. 1B shows a back view of the first vest style wearable, and FIG. 1C shows a front view of a second vest style wearable designed for a second body type, in accordance with some implementations.

FIGS. 2A and 2B are diagrams illustrating an example of the wearable article including containment portions, in which FIG. 2A shows the inner side and FIG. 2B shows the outer side, in accordance with some implementations.

DETAILED DESCRIPTION

Figure 2A:
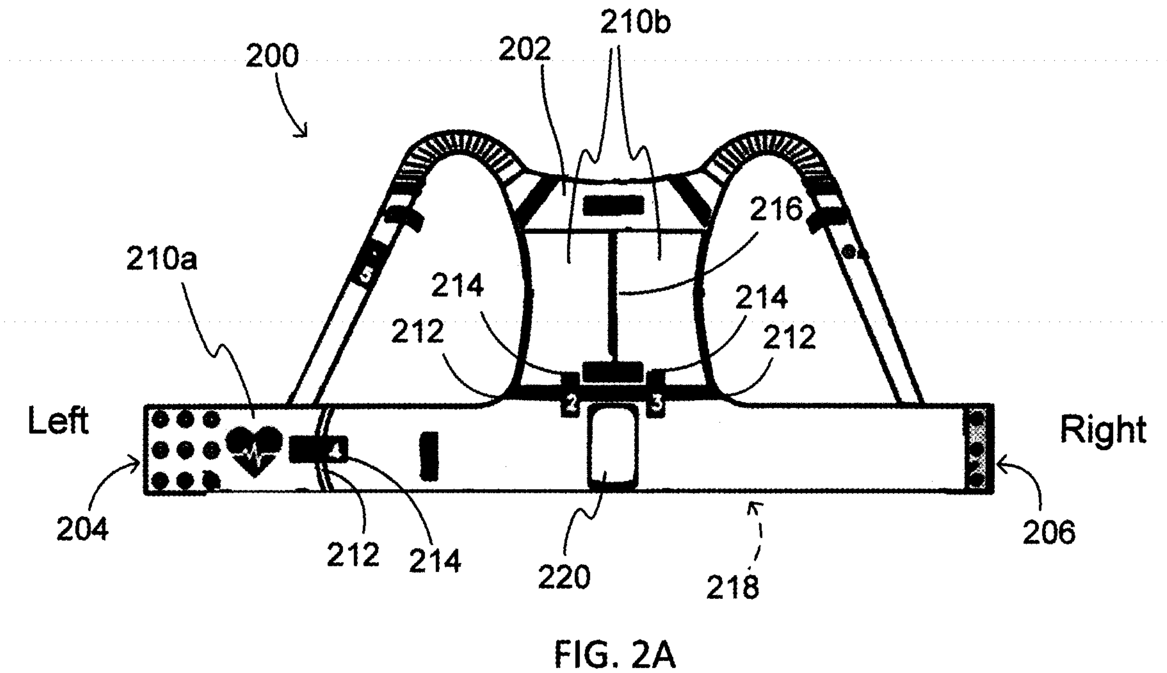

In the following description, various implementations are described. For purposes of explanation, specific configurations and details are set forth in order to provide a thorough understanding of the implementations. However, it will also be apparent to one skilled in the art that the implementations may be practiced without the specific details. Well-known features may be omitted or simplified without obscuring the implementations described. The description of the medical wearable article for containment of electrode pads provides a framework which can be tailored to individual systems built around the wearable medical device. Elements may be described in terms of “basic functionality” or varying degrees of functionality.

The present wearable article (also referred to as a “wearable” or “support structure”) is a wearable component of a medical device configured with elements to accommodate electrode pads in a manner that offers flexibility, cushion, and temperature regulation for comfort of a patient, as well as facilitating distribution of pressure on the electrode pads against the body of the patient. A containment portion of the wearable article houses the electrode pad and a spacer structure in a pocket or other separate, semi-separate, partitioned, semi-partitioned, isolated, semi-isolated or other discrete location of the wearable. The spacer structure, such as a three-dimensional (3-D) knitted material, is flexible to move as the body of the patient moves and yet provides a level of stiffness for pressure on the underlying electrode. The spacer structure is configured to provide a predictable spring force while establishing voids between springy elements for air to pass. The numerous springy elements dispersed in the spacer structure provide a thickness and open space for air circulation through the spacer structure, resulting in temperature regulation of the wearable article.

The present medical wearable may be largely made of a flexible base support material that maintains medical components for wear on the patient. The flexible support material can include various straps, belts, snaps, buttons, hook and loop, elastics, etc.

Other medical wearables may include materials that offer little breathability, especially in insulated areas located behind electrode pads, creating a heat prone section of the wearable article. Electrode pads require close body contact and can trap body heat. Furthermore, the electrode pads used for cardiac treatment can consume large areas of a patient body, creating large non-breathable areas. Components of other wearable devices that press electrodes against the body may further add to the temperature dysregulation. Wearable devices intended for long term wear by a patient may be particularly susceptible to temperature problems.

In contrast to the present wearable article, other wearable medical devices may be designed to increase electrode-to-body contact at the compromise of patient comfort. For example, other wearables may couple the electrode pad with blocks of nonbreathable or limited breathable material, such as closed-cell foam and open-cell foam. Closed-cell foam may include EVA (ethyl vinyl acetate), PE (Polyethylene), SBR (Styrene butadiene rubber), PU (Polyurethane), Latex, Neoprene, etc., such as foam materials commonly used underfoot in athletic shoes. Moreover, open-cell foam may not be sufficiently dense to enable pressure to be applied onto the electrode. Generally, foam can be chemically manufactured and may be molded, hot pressed, cold pressed, die cut, injected and/or machined.

By comparison with a foam material, the present spacer structure, such as a structure that includes knitted material, provides a breathable area within the containment portion of the wearable article and allows for circulation of air behind the electrode pad. Various layers of the spacer structure in the containment portion can provide compressibility and sufficient flexibility to enable the electrode to maintain contact with the body as the patient moves, including regular movements such as when the patient breaths in and out.

Evenly distributed pressure on the electrodes can improve the efficacy of shock treatment with the electrode, perhaps even allowing for use of lower energy shocks, which may in turn allow for a smaller battery and capacitor for the wearable medical device. The electrode needs to maintain good contact with irregular body surfaces or different body types and shapes, especially while the patient is active. To facilitate electrode to body contact under such conditions, the present spacer structures is able to mold to changing surface profiles. Springy characteristics of the spacer structure accommodates fluctuating contours.

Other benefits and features of the pressure system will be apparent from the further description of the system and methods, as described below.

The present wearable article of the medical device may be configured for continuous long term wear on the patient, for example wear on a torso of the patient for at least fourteen (14) days. Some implementations of the wearable article may be worn for a few months at a time. The term, "continuous" is understood to include daytime use, which may be from many hours of the day and full time at night, to full daytime hours and full nighttime use. In some implementations, the wearable article may be worn without stop except for temporary daytime removal during brief activities that may expose the wearable medical device to potentially adverse conditions. Such adverse conditions may include water contact, e.g., bathing or swimming, or for cleaning wearable article, etc. or for temporary period of non-use to repair/maintain the medical device. Thus, "continuous use" is intended to include such brief periods of non-use.

The electrode pad (also referred to as "therapy pad") employed with the wearable article is a component of the medical device that accommodates an electrode and an electronic interface to receive electrical inputs for the electrode to emit electrical pulses to the body of the patient. The electrode may be a thin pliable sheet of electrically conducting material, such as a metal, with one or more gel ejection ports. Additional elements of the electrode pad may include one or more fluid packs to store and release a fluid, e.g., gel, at the target treatment area of the patient. The electrode pad may also include a gas sack that receives and retains gas from a gas generator to apply pressure to the fluid pack during treatment of the patient. In some implementations, the spacer structure may be coupled to or integrated with the electrode pad. Additional features of the electrode pad is described below with regards to FIG. 8. Other types of electrodes and electrode pads are possible.

The patient for purposes of this description may also be referred to as a person, user, and/or wearer, who receives medical care in the form of treatment and/or monitoring by wearing the wearable article of the wearable medical device. The term "patient" for purposes of this description, refers to any person who uses any form, type, or style of the wearable article that includes one or more containment portions, according to the descriptions herein. The patient can be ambulatory, such that while wearing the wearable article the patient can walk around and is not necessarily bed ridden. The patient may be mobile to move from place to place with the assistance of another person or use of a mobility device, such as a walker, a cane, crutches, a scooter, a wheelchair, etc.

The particular context of these and other related terms within this description should be interpreted accordingly.

FIGS. 1A-1B show examples of wearable medical device 100 in which aspects of a wearable article 102*a*, 102*b* can be implemented and worn on various patients 104*a* and 104*b*. FIG. 1A shows a front view of a first vest style wearable article 102*a* designed for a first body type of patient 104*a*. FIG. 1B shows a back view of the first vest style wearable article 102*a*. FIG. 1C shows a front view of a second vest style wearable article 102*b* designed for a second body type of patient 104*b*.

The wearable article 102*a*, 102*b* includes a main body portion 106 formed of continuous or partially continuous outer materials to hold one or more medical device components onto the patient. The main body portion 106 may create a framework to which components or other sections of the wearable article may be attached or otherwise integrated with the main body portion, such as containment portions 108*a*, 108*b*, 108*c*, spacer structures, conductive layers, shoulder straps 110*a*, 110*b*, adjustable elements 114 (e.g., snaps to secure the belt and/or containment portions), pull tabs 116 (e.g., to open containment portions at insertion openings 126), elastic cord guide strips 118, hook and loop cord guide strips, elastic seams 120, etc.

Figure 2B:
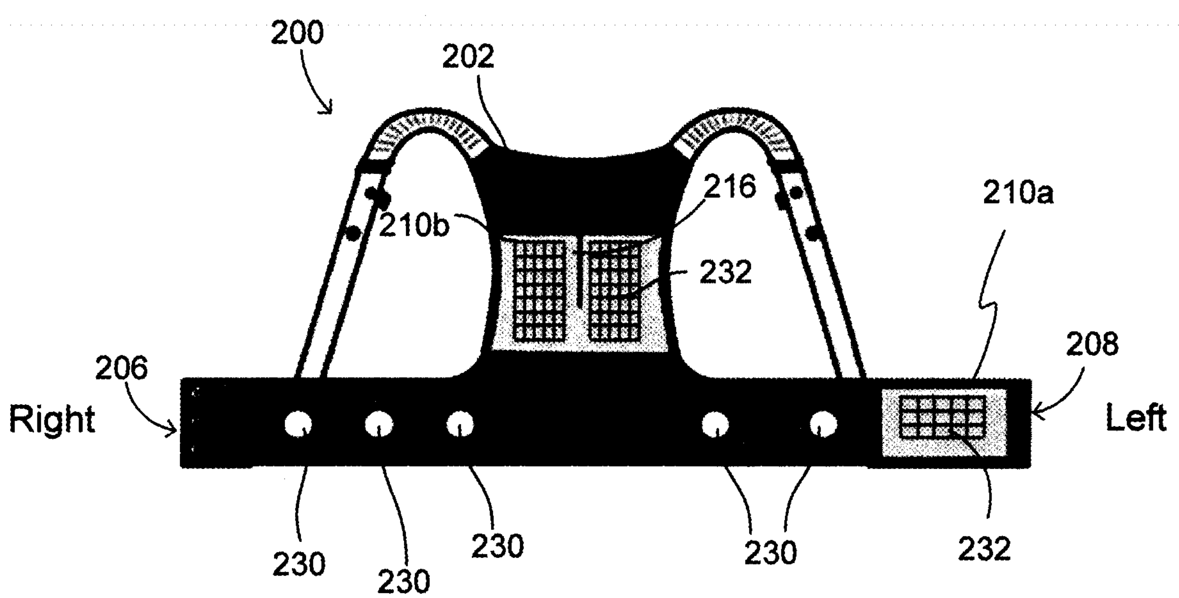

The main body portion 106 can include as a base material of the wearable article, e.g., one or more flexible support materials, such as a stretchy and breathable fabric material for overall comfort of the patient. In some implementations, an outer layer and an inner layer of flexible support materials may be sewn together to form a double layer of base material into which various components, such as monitor electrodes may be incorporated, as shown in FIGS. 2A, 2B, described below. The inner and outer layers may be the same material with same or similar characteristics or different materials with different characteristics. A single layer or more than two layers are also possible. In some implementations, one or more containment portions may be integrated with various layers of the main body portion, e.g., between the outer and inner layers. For example, the spacer structure may be coupled to, e.g., sewn onto, the outer layer. In some implementations, the spacer structure may be attached to the outer layer at a portion of the perimeter of the spacer structure and the remaining portion of the perimeter is unsecured. For example, two or three sides of the spacer structure may be attached to, e.g., sewn onto, the outer layer to form a pocket and one or two free sides. In this manner, the free sides of the spacer structure allow for flexibility of the outer layer to stretch around the electrode pad and secure the electrode pad against the body of the patient. The inner and outer layers may also define a space for enclosing leads or wires of the electrodes, and so on.

The flexible support material can form close to the body when the patient is active or at rest by various tightening components, such as elastic seams, shoulder straps 110*a*, 110*b* with adjustable features 112, belt 122 with adjustable elements 114, and various snaps, buttons, hook and loop, clasps, clamps, buckles, catchers, ties, etc. Other enclosures are possible. Such tightening components may additionally function to increase pressure onto the electrode pads for closer body contact.

In some implementations, the flexible support material of the main body portion 106 may have moisture wicking, breathable, compressive, and/or stretch characteristics, which may include synthetic fabrics, coatings, and additives (such as plastic, nylon, polyester, polypropylene, spandex, silver enhancement, recycled materials, etc. including variations thereof, e.g., LYCRA, DRI-FIT, SUPPLEX, TACTEL, MERYL, etc.), natural materials (such as bamboo, linen, TENCEL, and wool), or combinations thereof. Materials may be similar to swimsuit material or athletic material.

Certain areas of the main body portion 106 may include a stiffened material to strengthen support for component or other wearable article sections, such as containment portions 108*a*, 108*b*, 108*c*, snaps, etc. For example, in some implementations internal pressure may be generated within the containment portion, such as gas generated to deploy a fluid, e.g., gel, within fluid packs in the electrode pad. In such configurations, thickness of the electronic pad can increase within the containment portion. Stiffened material lining the exterior of the containment portion, as well as a spacer structure within the containment portion, may serve to increase and distribute the pressure of the therapy pad on the patient by resisting the pressure built up within the containment portion. The gas maintains the internal pressure after the gel is released and during shock treatment. The gas generator releases the gas shortly after detonating, e.g., within a second after detonating. The pressure within the containment portion may be maintained for an extended period of time, such as days or longer. There is an air pouch in the electrode pad that holds the gas and creates a static pressure for the electrode.

In some implementations, particular containment portions include a stiffened material lining such as containment portions that receive sufficient direct external pressure from the main body portion of the wearable article to ensure non-slippage of the electrode pad relative to the patient body. For example, a front containment portion 108*a* within an adjustable torso belt may be sufficiently tightened by providing tension in opposing directions that flexible support material is not needed at that containment portion to hold the electrode pad. Under these secure configurations of containment portions, the stiffened lining may be used as an outer layer of the containment portion. In other situations where tension is provided unevenly, such as in just one direction, there may be an imbalance of pressure on the electrode pad. In these uneven pressure situations, a stiffened material may not be employed. Instead, the wearable article may be configured such that flexible support material is in direct contact with the electrode pad, such as stretched around the electrode pad, to avoid slippage of the electrode pad.

Where the flexible support material is insufficiently tight or unevenly tight at the containment portion, for example by providing tension in one direction rather than opposing directions, additional support may be gained by employing the flexible support material to at least partially wrap around the electrode pad and hold the electrode pad against the patient. For example indirect, uneven, and/or insufficient pressure may be provided by shoulder straps on the back containment portions 108*b*, 108*c*. Such containment portions may be void of stiffened material or stiffened material may be limited in an area corresponding with the electrode pad. In this manner, the flexible support material can contact at least the borders of the electrode pad and provide a snug hold across the electrode pad.

Furthermore, where added flexibility is required, the spacer structure may be sized to be smaller than the face dimensions of the electrode pad to avoid blockage of the flexible support material to reach the perimeter of the electrode pad. For example, back containment portions may include spacer structures that are smaller than the electrode pad, where shoulder straps only create tension in one direction. By contrast, spacer structures in a front containment portion at the belt, which incorporates opposing even tension, may be various sizes relative to the electrode pad without restriction to accommodate the flexible support material, such as a spacer structure sized to the same or larger face dimensions than the dimensions of the electrode pad.

In the examples shown in FIGS. 1A-1C, the main body portion 106 of the wearable article 102 fits around a front side and back side of a torso of the patient 104*a*, 104*b*. Shoulder straps 110*a*, 110*b* and/or belt 122 may hold the main body portion 106, containment portion 108*a*, 108*b*, 108*c*, and electrode pads (when inserted) in place onto the torso of the patient 104*a*, 104*b*. In some implementations, the belt 122 includes adjustable elements 114 to enable the belt 122 to be tightened around the torso. The belt 122 may further include elastic seams along the length of the belt for additional constriction and support around the torso of the patient body.

The belt 122 may include one or more front containment portions 108*a*, which includes an internal spacer structure (not shown) and insertable electrode pad (not shown). The spacer structure may be positioned proximal to the electrode pad to transfer and distribute pressure from the belt when tightened (e.g., pressure created by the tightening structures) to the electrode pad. Additional details of the containment portions is described below with regards to FIGS. 3-4.

The vest style wearable article 102 can include two shoulder straps 110*a*, 110*b*, one over each shoulder of the patient 104*a*, 104*b* extending from the front side of the patient to the back side of the patient and coupled to the main body portion 106. In some implementations, the wearable article may also be implemented with a single shoulder strap, for example, that may wrap around the neck, or around one shoulder at an angle, or as a full vest rather than having shoulder straps.

The front view of the wearable article 102*a* of the first vest style, shown in FIG. 1A includes long shoulder straps 110*b* coupled to the belt 122 that fits below the breasts of the patient. The front view of the wearable article 102*b* of the second vest style, shown in FIG. 1C includes short shoulder straps 110*b* coupled to frontal sections 124 of the main body portion 106 that fit over breasts of the patient. The frontal sections 124 are coupled to the belt 122 below the breasts of the patient. Other designs of wearable articles are possible.

The back side view of the wearable article, as shown in FIG. 1B, the main portion may couple with the shoulder straps on the back side of the patient. In this manner, the wearable article 102*a*, 102*b* may encircle the patient without a need for adhesives to attach the wearable article onto the patient. The back of the wearable article may include one or more back containment portions 108*b*, 108*c* to house electrode pads, as described with detail below with regards to FIG. 4.

The wearable medical device 100 includes electrode pads which, in some implementations, may be removably inserted into containment portions 108*a*, 108*b*, 108*c* of the wearable articles 102*a*, 102*b*. One or more electronics systems such as electrical controls to the electrode pads are shown in detail in FIG. 8, described below.

The wearable article may further include a removable control hub 130 to communicate with electronic components of the wearable device, for example via cords 132. The wearable article may include external access to electrical components, such as through insertion openings 126, so that cables and cords 132 may be strung on the outside of the wearable article and away from the body of the patient.

There may be other components of the wearable medical device 100, which are not shown, such as a power source, various sensors coupled to the wearable article 102 or otherwise associated with the patient, input/output interfaces, such as a display screen, microphone, keypad, touchpad, button or switch, network interface, etc. Various components, including electronic components including sensors, batteries, electrodes, and cables, may be detached from the wearable article, for example, to wash the wearable article, repair, or replace the wearable article.

The depictions in FIGS. 1A, 1B, and 1C are not to be construed as limiting how the wearable article is implemented or worn. It will be understood that the wearable article 102*a*, 102*b* is shown only generically in the figures, and in fact partly conceptually. FIGS. 1A, 1B, and 1C are provided merely to illustrate concepts about wearable article and is not to be construed as limiting how the wearable article is implemented, or how it is worn.

The wearable article can be implemented in many different ways to engage with at least a portion of the torso of the patient and provide for long term continuous monitoring of the patient. For example, it can be implemented in a single element or a combination of multiple elements, which may be coupled together. In some implementations, the wearable article could include a vest, a half-vest, or other type of garment that engages with at least a portion of the torso. In some implementations, wearable article 102 could include a harness, one or more belts or straps, etc. that fit on a torso or other accessible parts of the patient. The wearable article can also be worn around hips, over the shoulder, around appendages, etc. In implementations, such items can be worn similarly to analogous articles of clothing. Such items can be worn parallel to or underneath other articles of clothing.

In some implementations, the wearable article can be worn by being attached to the patient's body by adhesive material, for example as shown and described in U.S. Pat. No. 8,024,037. The wearable article may also be implemented as described in U.S. Patent Application No. US2017/0056682.

FIGS. 2A and 2B are diagrams illustrating various sides of an example of the wearable medical device 200 employing a wearable article 202 shown flat. FIG. 2A shows the outer side of the wearable article that is seen when worn by a patient. FIG. 2B shows an opposite inner side of the wearable article that contacts the body of the patient when worn. To be worn, the left end 204 and right end 206 can be brought together while surrounding the torso, and affixed to each other, either at their edges or partly overlapping. Appropriate mechanisms can hold together the ends 204, 206, such as snaps, buttons, elastic ties, zippers, hooks and loops, and so on.

The wearable article has containment portions 210*a* (front), 210*b* (back) to house electrode pads. Insertion openings 214 of the containment portions 210*a*, 210*b* including pull tabs 214 on the outer side of the wearable article to pull open the containment portions for ease of access, even when wearing the wearable article. The containment portions may hold one or more electrode pads as a single (as in front containment portion 210*a*) double (as in back containment portion 210*b*, triple, etc. Front containment portion 210 may be positioned along a belt 218.

A double back containment portion 210*b* may have one or more barriers 216 that at least partially separate two areas for individual electrode pads. As such, a double containment portion may also be referred to as simply a containment portion that holds two electrode pads or as two single (divided) containment portions, each holding a single electrode pad. In some implementations, the barrier 216 may be sewn into the fabric of the containment portion. The wearable article 202 may include additional features to hold or house medical device components, such as hub pocket 220.

In FIG. 2B, the wearable article 202 of the wearable medical device 200 may employ components for monitoring, such as multiple sensing electrodes 230 and/or treatment such as therapy electrode pads in containment portions 210*a*, 210*b*. Where too much electrical noise is produced by therapy electrodes for analyzing the ECG signal, the multiple sensing electrodes 230 and therapy electrode pad may be separate. In some implementations, electrode pads in containment portions 210*a*, 210*b* may be used for both therapy treatment and monitoring.

Multiple ECG sensing electrodes 230 define different vectors for sensing ECG signals along different ECG channels. These different ECG channels therefore present alternative options for analyzing the patient's ECG signal. The patient impedance along each ECG channel may also be sensed. In the example of FIG. 2B, multiple ECG sensing electrodes 230 protrude from the inside surface of the wearable article 202. These ECG sensing electrodes 230 can be affixed to the inside surface of the wearable article 202, while their leads or wires can be located mostly or completely within the wearable article 202.

ECG sensing electrodes 209 may be intended to contact the skin of the patient when the wearable article is worn. The sensing electrodes 209 can be made from suitable material for good electrical contact, such as a metal, for example, silver.

Electrically conducting linings 232 may be disposed in the interior side of the containment portions 210*a*, 210*b*. The conducting linings can be a mesh made from flexible material such as loose netting, and so on. The electrode pads can be placed in containment portions 210*a*, 210*b* and contact the skin of the patient through the respective electrically conducting linings 232. The electrical contact can be facilitated by conductive fluid, e.g., gel, that can be deployed in the area when the time comes for a shock.

Figure 3:
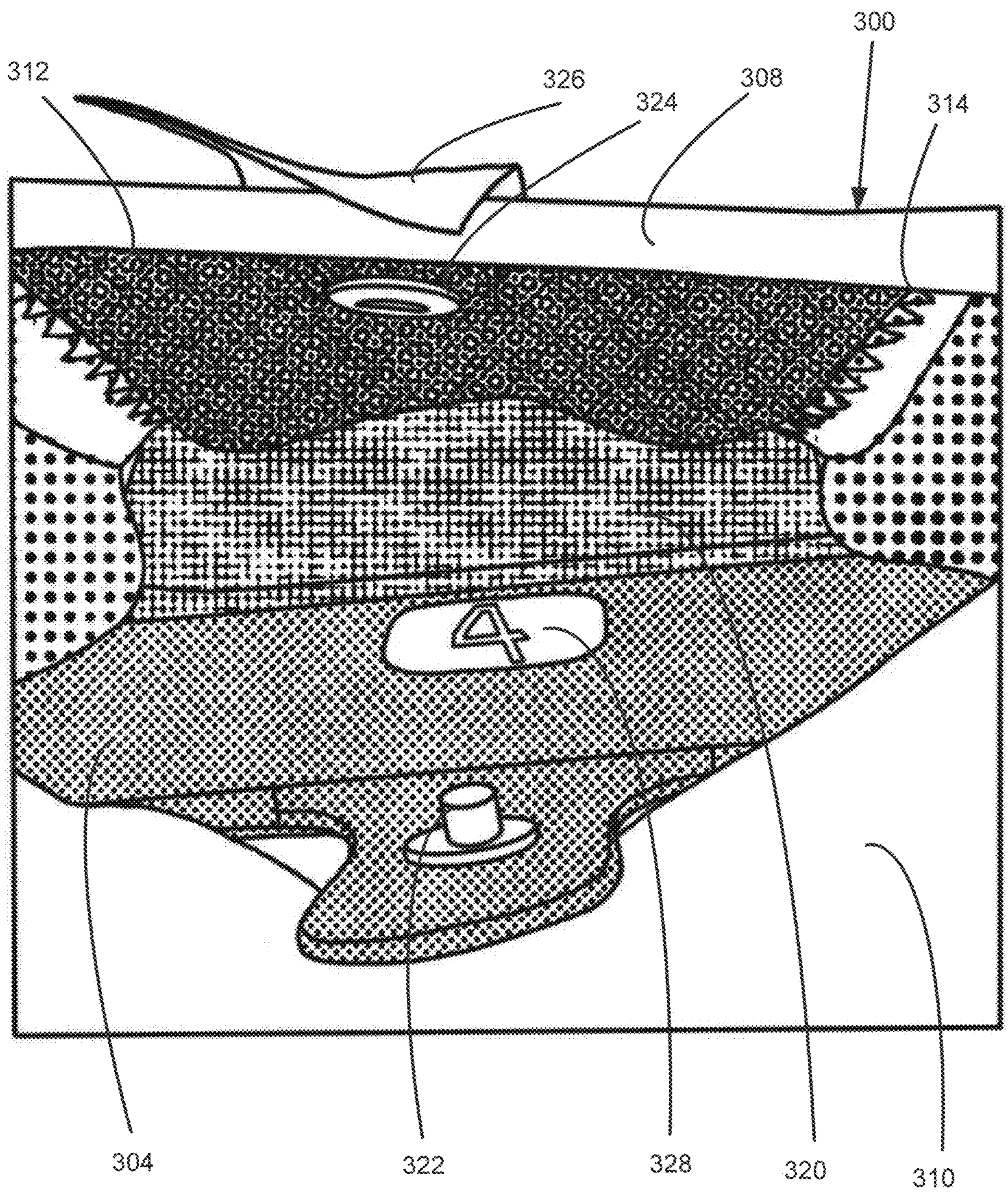
FIG. 3 is a diagram illustrating a partial inside view of an example single containment portion of a wearable article with inserted electrode pads, in accordance with some implementations.

FIG. 3 is a diagram illustrating a partial inside view of an example single containment compartment 300 of a wearable article, as seen through an insertion opening 302 and containing an inserted electrode pad 304. The containment compartment 300 may include components sandwiched between an outer layer 308 and an inner material (not shown) configured to be positioned in contact with both the patient and the electrode pad.

The outer layer 308 may be flexible support material contiguous to or adjoined with the main body portion of the wearable article, and where the containment compartment may be defined by stitching in the flexible support material or other border material. In some configurations, the outer layer 308, may resist pressure increased within the confinement portion in conjunction with the spacer structure to enable the electrode pad to be pressed against the patient, or the outer layer 308 may transfer pressure from outside of the confinement portion to the spacer structure and towards the electrode pad. The spacer structure 312 may be proximal to (e.g., sewn to) the outer layer, such as a stiffened outer layer.

In some implementations, the inner material of the containment compartment may be an electrically conducting lining underneath the electrode pad 304. In some implementations, the electrically conducting lining may be sewn to or otherwise attached to an inner layer 310 of the flexible support material of the main body portion of the wearable article. In some implementations, the electrode of the electrode pad serves as the inner material of the containment portion for the electrode to make direct contact with the patient (typically with application of fluid at the site). For example, the electrode pad may be pressed into a holding structure of the containment portion without the electrode sitting on a separate inner material.

The spacer structure 312 may be coupled to the outer layer 308 by stitching 314 along at least one perimeter of the spacer structure 312. In some implementations, the spacer structure 312 is rectangular and is stitched to the outer layer along two of four sides of the spacer structure. The spacer structure may be generally a shape that corresponds with the shape of the electrode pad 304. The spacer structure may be sized relative to the size of the electrode pad, e.g., same size, similar size, larger or smaller in size as the electrode pad.

In some implementations, one or more fluid packs 320 may be provided on the electrode pad 304 or other location proximal to the electrodes. A fluid, such as a gel, can be stored in fluid pack 320 and deployed between the electrodes and the patient's skin. The fluid is preferably conductive, such as by including an electrolyte, for making a better electrical contact between the electrode and the patient's skin. Saline and a hydrogel are some examples. When the fluid is deployed, the electrical impedance between the electrode and the skin is reduced. The fluid may have higher viscosity than water, such as by being a gel, so that it does not flow away, after it has been deployed. The fluid can be used for one or both therapy electrodes and ECG monitoring electrodes. In some implementations, the spacer structure 312 may provide compressible resistance to pressure built up within the containment portion from a gas injected into a gas sack adjacent to or integrated with the fluid pack 320.

Containment portion 300 may include a fastener such as snap stud 322 corresponding to snap socket 324 and opened with the assistance of pull tab 326. An electrode pad identifier 328 may assist the patient in inserting the proper electrode pad into a corresponding containment portion 300.

Figure 4:
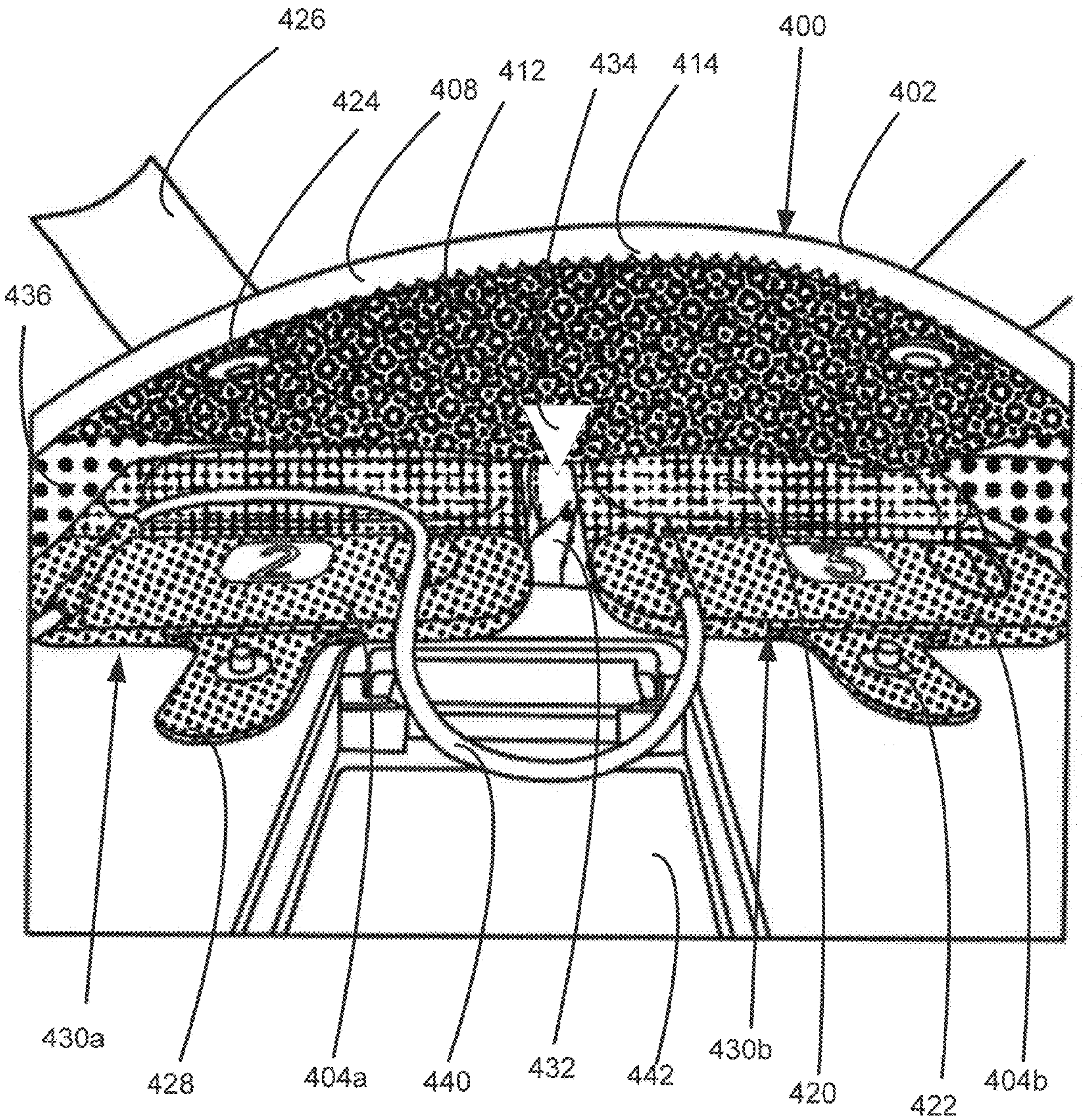
FIG. 4 is a diagram illustrating a partial inside view of an example double containment portion of a wearable article with an inserted electrode pad, in accordance with some implementations.

FIG. 4 is a diagram illustrating a partial inside view of an example double containment compartment 400, as seen through an insertion opening 402 with inserted electrode pads 404*a*, 404*b* of a wearable article. A cable (e.g., wire) 440 may connect to each electrode pad and or fluid pack 420. An outer layer 408 of flexible support material of the main body of the wearable article may attach to spacer structure 412 by stitching 414 or other coupling mechanism (such as adhesives, hook and loop, etc.).

A barrier 432 may separate the containment portion into two sub-compartments 430*a*, 430*b*. In some implementations, the spacer structure 412 may be a single material divided into separate structures within each sub-compartment by barrier stitching 434 (such as barrier 216 in FIG. 2A) through the spacer structure and outer layer 408 of the wearable article. Barrier stitching 434 may also run through electrical conducting mesh 436 or other bottom layer of the containment portion.

In some implementations, each sub-containment may include a snap stud 422 positioned on flap 428 to facilitate closure with corresponding snap socket 424. Other wearable article components may include a hub pocket 442 for removeably inserting a control hub.

Figure 5:
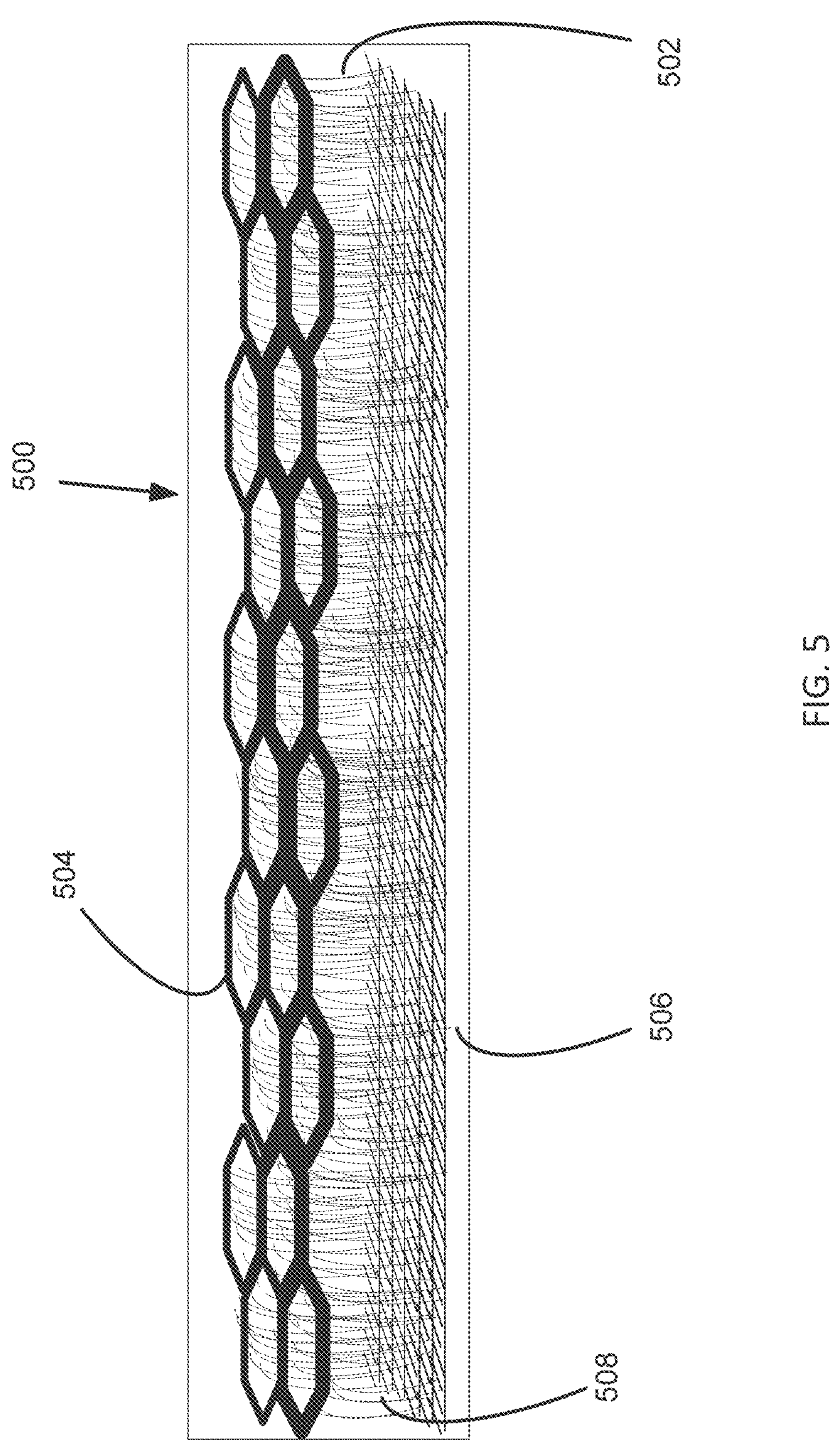
FIG. 5 is a cut away diagram illustrating an example of a spacer structure including a compressible middle layer, in accordance with some implementations.

FIG. 5 is a cut away diagram illustrating an example of a spacer structure 500 including a compressible middle layer 502 between a top layer 504 and bottom layer 506. The middle layer 502 includes a plurality of springy elements 508 coupled to the top layer 504 at one end of the springy elements and coupled to the bottom layer 506 at the other end. The spacer structure 500 generally has one or more characteristics including being breathable, resilient, and providing cushion.

The middle layer 502 may be sized to a particular thickness that is sufficient to provide compressibility of the containment portion without having too much volume such that the springy elements 508 extending between upper and bottom layers are caused to buckle or become floppy or otherwise fail to spring back to a target shape once compressed. For example, the middle layer 502 of the spacer structure 500 may be between about 2 mm to 15 mm thick and such as about 8 mm in thickness The spacer structure may include sufficient packing of springy elements, for example a density of about 450 g/m$^2$. The springy elements may include a plurality of filaments, such as yarns, coils, or other resilient material. Various materials may be used to form the springy elements including polyester, nylon, metals, etc.

In some implementations, the spacer structure may be a 3-D spacer mesh in which the top layer and/or the bottom layer include a knitted mesh, and the plurality of springy elements include a plurality of knitted filaments. The springy elements may be knitted to vertically extend between the top permeable layer and the bottom permeable layer. The springy elements may be attached to one or both of the top and bottom layers. Example spacer structures include 3-D spacer fabric available from Bowi-Style, Poland.

The individual spring elements 508 of the middle layer 502 may be spaced apart from one another to allow for air flow through the middle layer 502. In some implementations, the top layer 504 and/or bottom layer 506 may also be permeable such that air may circulate through the layers. In other implementations, one or both of the top and bottom layers 504, 506 may resist fluid flow, including impermeable or semi-permeable materials such as a tight or solid knit, weave, or other solid material. Example knitted mesh patterns are described below with regards to FIGS. 6A and 6B. In some implementations, the top and/or bottom layer may be more rigid than the middle layer to provide stiffness and facilitate pressure against the electrode pad. In some implementations, one or more materials of the spacer structure material may be resistant to moisture absorption and/or include anti-microbial elements, such as silver, copper, or zinc. The top and/or bottom layers may be the same, similar or different material as the springy elements of the middle layer.

Typically, the spacer structure is washable so that the spacer structure may remain intact on the wearable article for washing of the wearable article. However, in some implementations, the spacer structure may be separately removeable for replacement and/or reinsertion into the containment portion.

In some implementations, the middle layer 502 may be coupled to an outer layer of the containment portion to resist pressure increase within the containment portion, thereby enabling pressure to be exerted onto the at least one electrode pad in a direction toward the patient. Coupling of the middle layer directly to the outer layer may be through stitching, adhesives, hook and loop, other fasteners, etc.

Figures 6A, 6B:
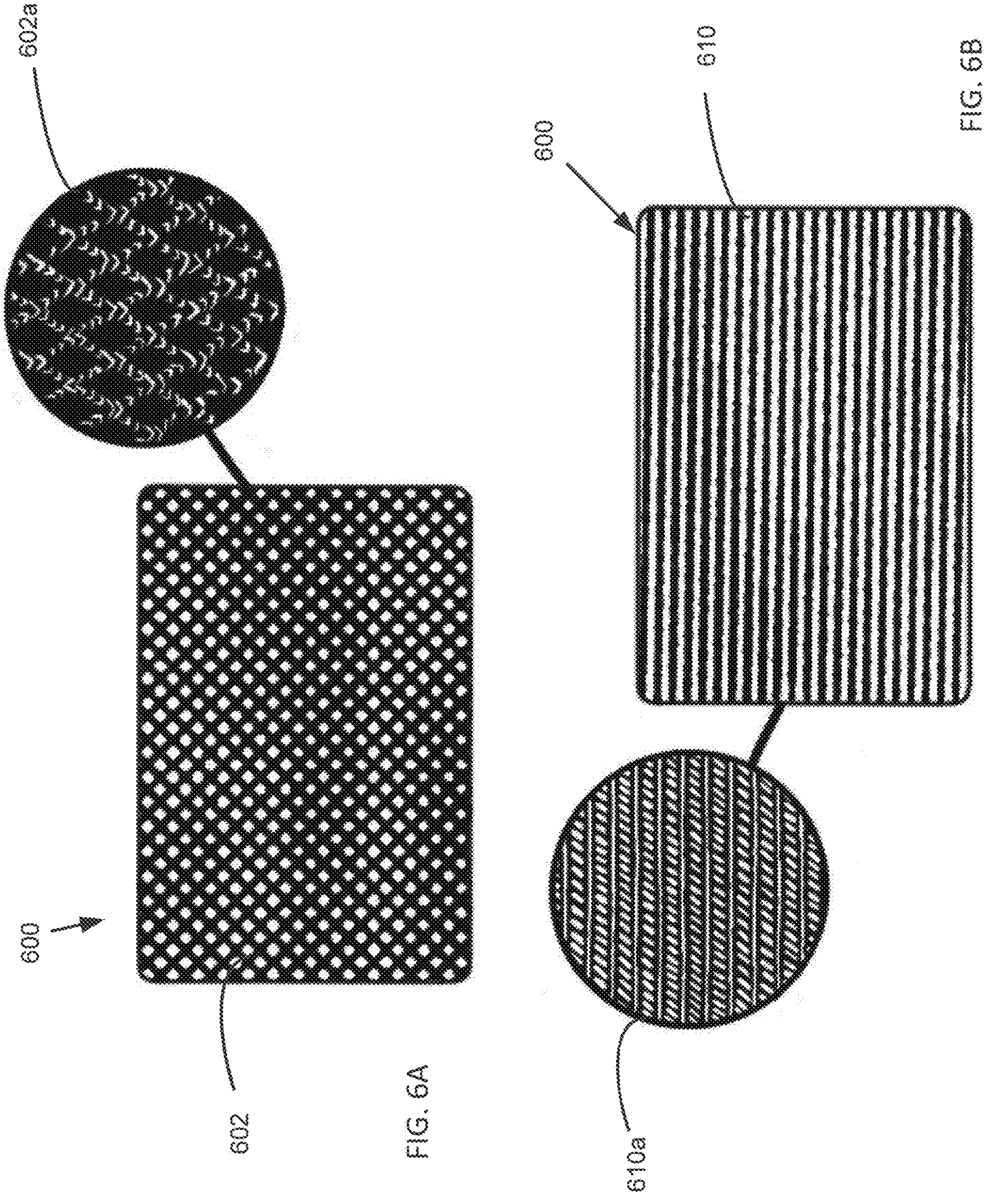
FIGS. 6A and 6B are diagrams illustrating an example of a spacer structure in which 6A shows a top permeable layer and 6B shows a bottom permeable layer, in accordance with some implementations.

FIGS. 6A and 6B are diagrams illustrating permeable layers of an example spacer structure 600. As shown in FIG. 6A as a top down view of the spacer structure 600, the top permeable layer 602 may be a knitted pattern with a diamond knitted design, as shown in greater detail in zoomed-in view 602*a*. In some implementations of the spacer structure 600 in use, the top layer 602 may be attached, e.g., sewn, onto the outer layer of the containment portion, such as a flexible support material of the main body portion of the wearable article.

FIG. 6B shows a bottom up view of the spacer structure 600 with a bottom permeable layer 610 having a knitted pattern of knitted longitudinal lines extending across the spacer structure 600 and with knitted diagonal lines running between the longitudinal lines. The pattern is shown in greater detail in zoomed-in view 610*a*. Illustrated in respective zoomed-in views 602*a* and 610*a*, the longitudinal line pattern 604 of the top layer is tighter than the bottom diamond knitted design 612. However, both top and bottom patterns are loose enough for air flow through the layers.

Other patterns may be employed in the top and bottom layers with varying permeability characteristics. For example, in some implementations the top and bottom layers may have a same or similar pattern. In some implementations, the patterns may be opposite of that shown in FIGS. 6A and 6B so that the longitudinal line pattern 604 may be on the bottom layer and the bottom diamond knitted design 612 may be on the top layer.

In some implementations, the top and/or bottom layers of the spacer structure may be formed from a solid material, such as a tightly woven fabric, plastic, or other solid material. In such configurations, the middle layer provides for air circulation in a path through the middle of the spacer structure rather than the top and bottom layer adding to air circulation paths.

Figure 7A:
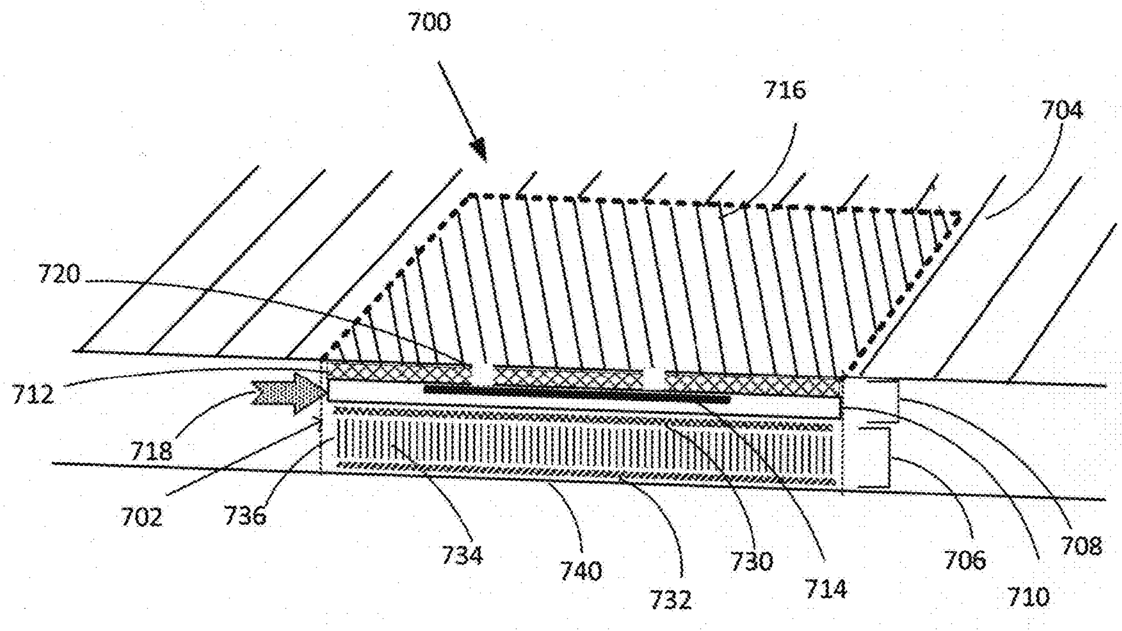
FIGS. 7A and 7B are cross-sectional diagrams illustrating examples of a compression portion of a wearable article including a spacer structure, fluid pack, and electrode pad, in which 7A shows the compression portion in a steady state and 7B shows the compression portion in a prepared state ready to perform shock treatment, in accordance with some implementations.
Figure 7B:
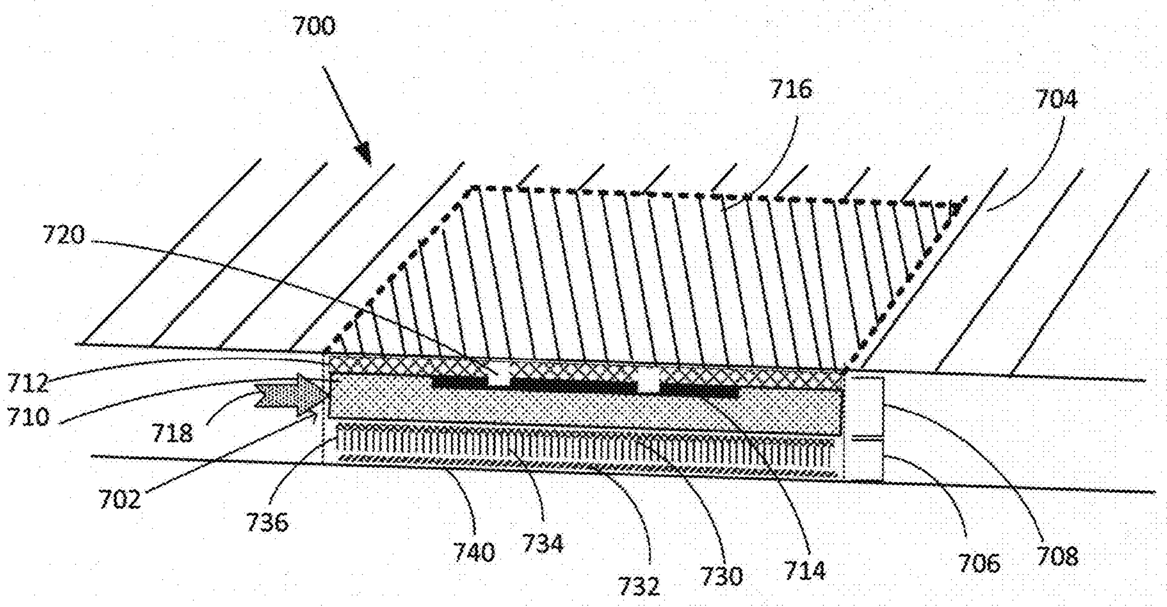

FIGS. 7A and 7B are cross-sectional diagrams illustrating an example of a compression compartment 700 during different times wear. In FIG. 7A, the wearable article is in a steady state in which the compression compartment has not been prepared to perform shock treatment on the patient body. In the steady state, the health parameters of the patient may be monitored, such as with monitoring electrodes, sensors, and/or other data. In FIG. 7B, the wearable article is in a prepared state, ready to perform shock treatment on the patient.

FIGS. 7A and 7B show a confinement portion 702 coupled to a flexible support material 704 of the main body portion of the wearable article. The confinement portion 702 includes a spacer structure 706 attached to an outer layer of the wearable article, e.g., flexible support material, a fluid pack 710 integrated into the electrode pad 708 at a side opposite of the electrode 712. The spacer structure 706 includes a bottom layer 730 proximal to the electrode pad, a top layer 730 proximal to an outer layer 740 of the containment portion, and a middle layer 734 with a plurality of springy elements 736.

The fluid pack 710 holds fluid 714 to be ejected at the body of the patient at the point of contact of the electrode 712 with the body. The electrode pad 708 is inserted into the containment portion 702 with the electrode 712 pressing against an electrically conducting mesh 716. The electrode pad is also coupled to a gas inlet 718 to inject gas when triggered just prior to shock treatment, into the fluid pack 710 and/or into a gas sack adjacent to the fluid pack 710.

As shown in FIG. 7B, injection of gas causes an increase in pressure within the containment portion 702. The fluid pack 710 may expand to press against the spacer structure 706. In response to the pressure increase, the spacer structure 706 compresses at the middle layer to somewhat absorb and yet resist the pressure increase. The thickness of the spacer structure decreases when the pressure builds within the containment portion and the springy elements 736 compress.

Subsequent to the filling of gas, the fluid 714 is forced out of port holes 720 in the electrode 712. In some implementations, the gas pressure is maintained after the gel is released from the fluid pack during the therapy treatment. The gas can also remain within the gas sack for a period of time post treatment. In this manner, pressure within the containment portion remains at a high level against the spacer structure 706 and electrode to ensure non-slippage of the electrode against the body of the patient during treatment.

In some implementations, after the electrode applies shock treatment, the pressure may be gently released, causing the spacer structure to re-expand to its original thickness and shape due to the resiliency of the spacer elements 736 in the middle layer 734. The electrode pad may be removed from the containment portion to be replenished with fluid for future treatments.

In some implementations, the fluid 714 may be constrained within a separate chamber in the fluid pack 710 rather than freely sitting in the fluid pack. In still some implementations, the fluid pack contains the fluid and the gas may be ejected into a confined space of a gas sack between the fluid pack and the spacer structure to expand against the spacer structure and press against the fluid pack, thereby ejecting the fluid.

Details of example fluid packs and processes to release the fluid may be found in U.S. Pat. No. 11,464,991, the contents of which is incorporated herein by reference.

Figure 8:
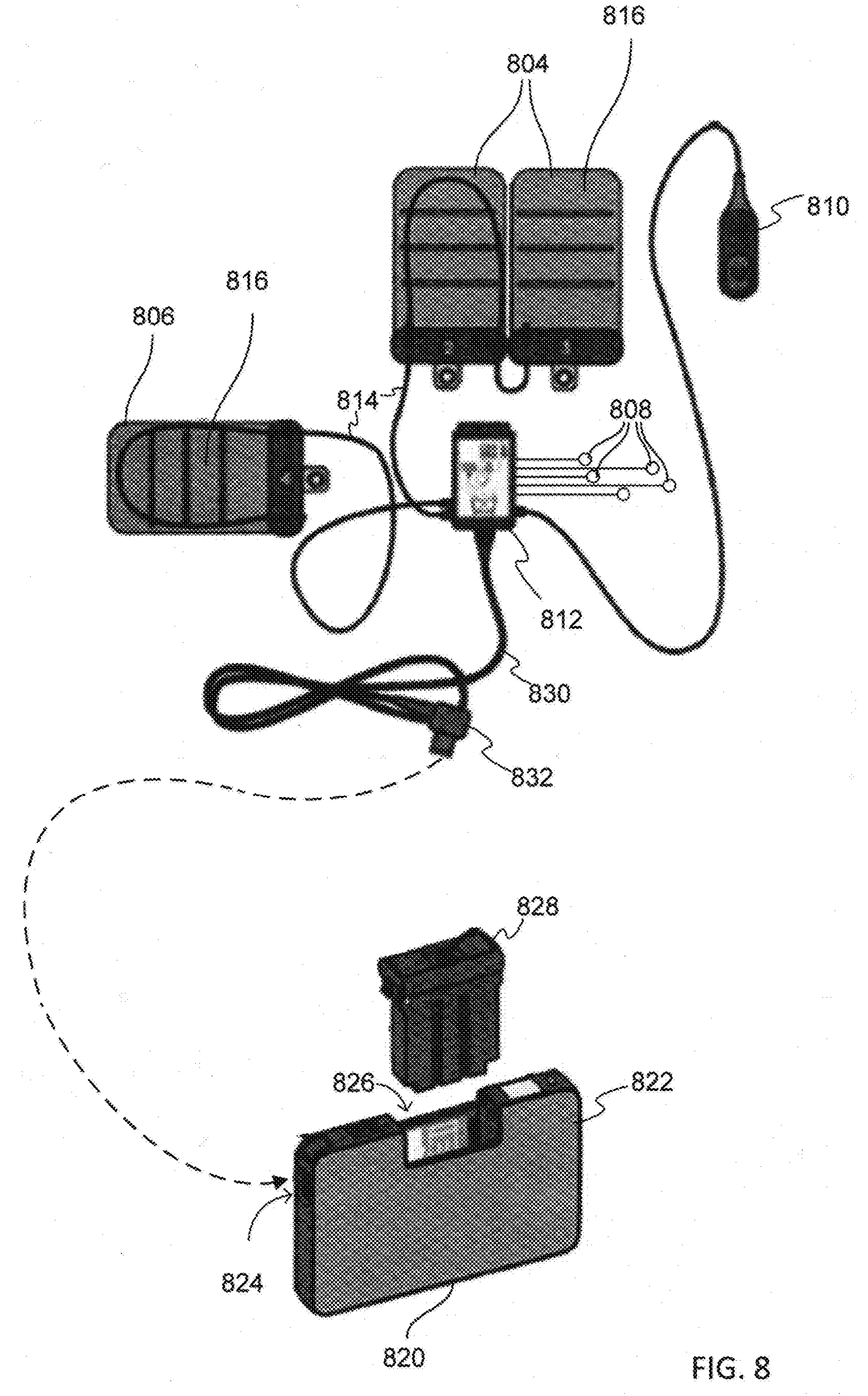
FIG. 8 is a diagram illustrating an electrical system including electrode pads for use with the wearable article, in accordance with some implementations.

FIG. 8 shows sample electronic components assembly 800 that can be used with the wearable medical device. The components include a unit 802, back therapy pads 804 and a front therapy pad 806, monitoring electrodes 808, an alert device 810, all coupled to a hub 812 by respective cables

814. For instance, the alert device 810 can be used by the patient to notify the system that the patient is actually alive and an imminent shock is not actually needed, which may otherwise happen in the event of a false positive detection of a shockable heart rhythm of the patient.

The front therapy electrode pad 806 can be inserted into the front confinement portion 108*a* of FIGS. 1A-1C, while the back therapy electrode pads 804 can be inserted into the back confinement portions 108*b*, 108*c* of FIGS. 1A-1C. A shock is generated between the therapy electrode pads 804, 806 taken together as the therapy electrode pads 804, 806 are electrically connected to each other. The therapy electrode pads 804, 806, have leads which can be configured to be coupled to the hub 812. The therapy electrode pads 804, 806 include fluid packs 816 at an ejection side of the electrode pads that is opposite of a metal shock emitting side. ECG sensing electrodes 808 and respective wires or leads can be configured to be coupled to the hub 812.

Figure 10:
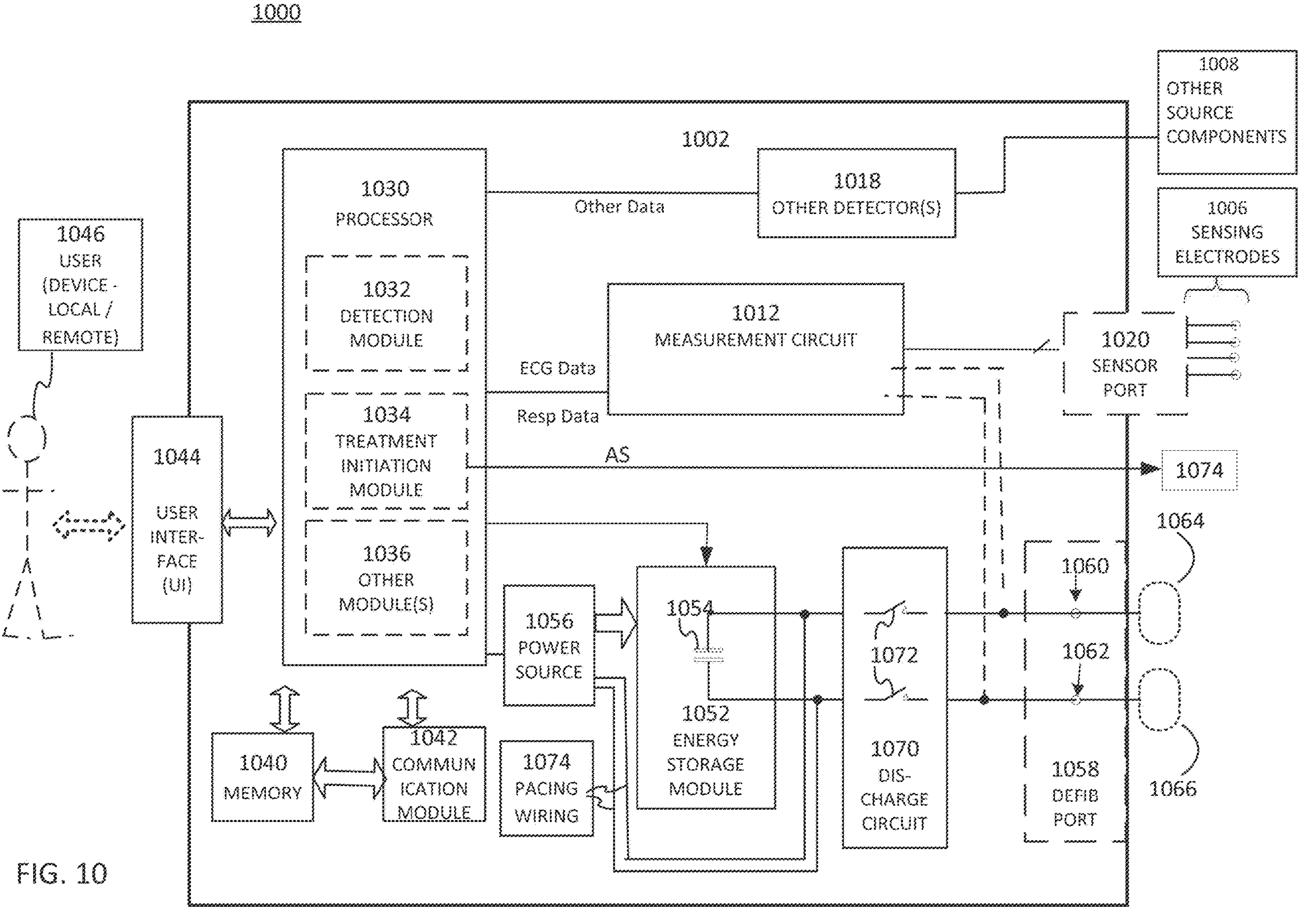
FIG. 10 is a diagram illustrating an example of an electronics system including electrode pads for use with the wearable article, in accordance with some implementations.

A unit 820 can implement many of the functions of the unit 1002 of FIG. 10. However, some of the functions of the unit 1002 of FIG. 10 are implemented instead by the separate hub 812, which can be connected to the 820 through a hub cable 830 and hub plug 832. The hub 812 is generally smaller and lighter than the unit 820. Hub 812 can be detachably coupled to the wearable article and can accommodate multiple electrical connections to other components on the wearable article.

The unit 820 may be carried and used by the patient away from the wearable article, such as by a separate carry container, and detachably coupled to the hub 812. The unit 820 has a housing 822 and a hub plug receptacle 824 at the housing 822. The unit 820 may also include a battery opening 826 configured to receive a removable battery 828. The unit 820 may also include devices for implementing a user interface such as a monitor screen, speaker, vibrating mechanism, and so on.

Figure 9:
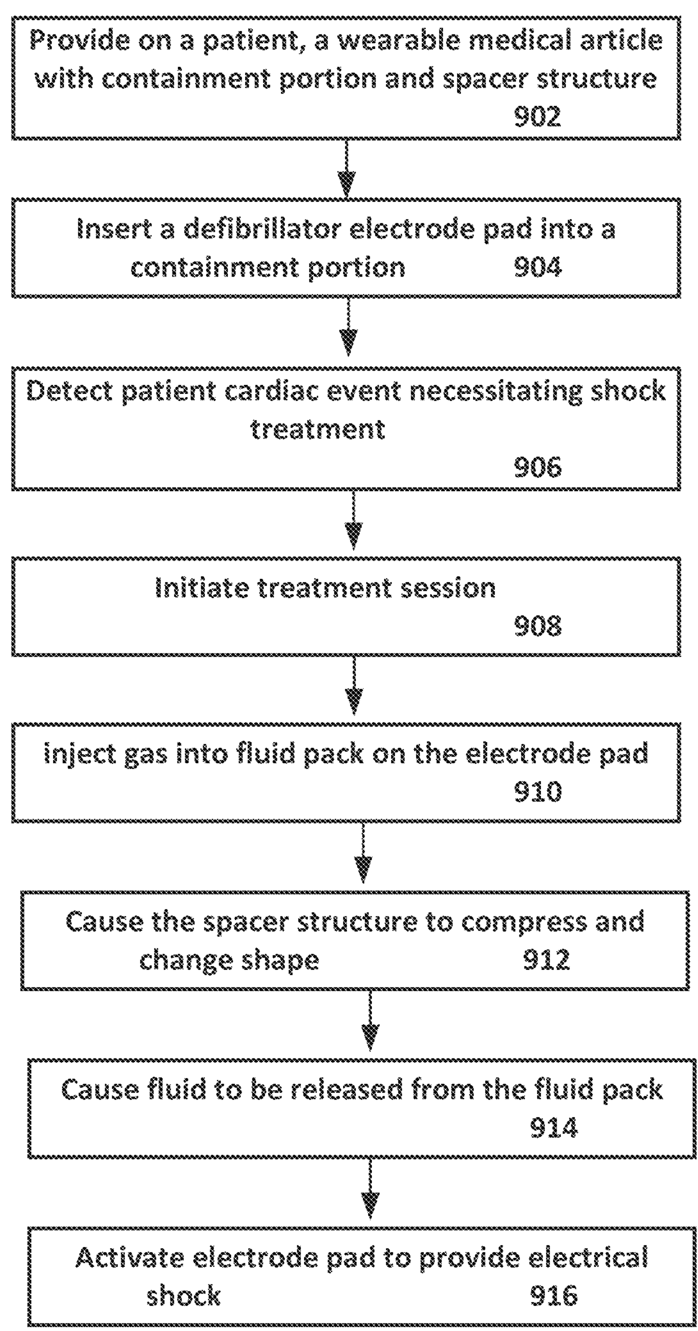
FIG. 9 is a flowchart of a defibrillation process using the wearable article, in accordance with some implementations.

FIG. 9 shows a flowchart of an example defibrillation process 900 performed by the wearable medical device using at least some of the components described herein. In block 902 the wearable article is provided with one or more containment portions, each having an attached spacer structure, and other components described above with regards to FIGS. 3-7.

In block 904, a defibrillator electrode pad is inserted into a containment portion of the wearable article. The insertion of the electrode pad may be performed as the wearable article is worn by the patient or prior to the patient putting on the wearable article.

In block 906, a patient cardiac event is detected that necessitates shock treatment of the patient. Detection of patient health parameters and determination of the treatment needs can be performed by various sensors and processors of the medical device, for example, as described below with regard to FIG. 9. Examples of detection and determination processes that may be employed by the present wearable medical device and wearable article are described in U.S. Pat. No. 9,757,581, issued Sep. 12, 2017 and U.S. Pat. No. 11,052,241, issued Jul. 6, 2021, the contents of which is incorporated herein by reference. In block 908, a treatment session is initiated and the wearable medical device is prepared to perform shock treatment.

In block 910, as part of the treatment session, gas is injected into a fluid pack and/or separate gas sack in the electrode pad within the containment portion. In block 912, the injected gas causes an increase of pressure within the containment portion and, as a result, causes the spacer structure to compress and change shape.

In block 914, the increase of pressure causes fluid stored in the fluid pack to be released through the containment portion and onto the body of the patient at a contact point with the electrode of the electrode pad. The fluid may be a liquid, gel, or other substance to assist with electrical conduction that is different from the gas released into or next to the fluid pack. The gas may be air or other inert gas. In some implementations, the gas is contained in the gas sack remains as the fluid is released to at least substantially maintain pressure in the containment portion during the electrical shock treatment. In block 916, the electrode of the electrode pad is activated to provide electrical shock.

When the electrical shock treatment is completed, the gas injection is ceased. The gas may slowly, over days or weeks, seep out of the gas sack. The wearable article is then free to be removed from the patient and the electrode pad removed from the containment portion to be replaced with electrode pads that are ready for use. Removal of the electrode pads from the wearable article decreases pressure in the containment portion and causes the spacer structure to decompress into an original shape or similar to the original shape.

The wearable article may be washed, e.g., placed in a washing machine, while the spacer structure is still attached to the containment portion of the wearable article. In this manner, the wearable article may be prepared for future use by the patient. In some implementations, when a patient is finished using the wearable medical device, the electrode pad is reused for a next patient and the wearable article and spacer structure is not reused on different patients for hygienic purposes. For reuse, it is advantageous for the electrode pad to be unbound to components intended for single patient use, such as the spacer structure.

One or more steps of the defibrillation process 900 may be performed under the control of one or more computer systems configured with executable instructions and/or other data, and may be implemented as executable instructions executing collectively on one or more processors, for example, as described below with reference to FIG. 9. In some implementations, defibrillation process 900 may include additional steps or less steps, and the steps may be performed in various orders.

FIG. 10 shows an example of an electronics system of the wearable medical device 1000 including electrode pads for use with the wearable article. The unit 1002 is intended to represent one or more units that perform functions on health signals or health data. Functions of the unit(s) can include one or more of collect signals representing various health parameters relevant to the health of a patient from signal source components generate health data associated with the signals, determine potential or actual health events, initiate defibrillation shock treatment sessions, release gas for electrode shocks, etc. The unit 1002 may also perform additional functions and combinations of these functions. Functions of unit 1002 as depicted may also be performed by multiple units 1002, each of which perform sub combinations of the functions.

Signal source components include sensors and/or transducers, to collect health signals associated with health parameters relevant to assessment of the patient for health events. Health parameters may include any combination of patient physiological parameters, patient state parameters, system parameters, and environmental parameters. Other types of signal source components are possible, including clocks to track time and date. Signals from the various source components feed into detectors for processing and generating associated health data.

Sensing electrodes 1006 may produce signals for ECG interpretations and for respiration assessments. Sensing electrodes 1006 may be one or more transducers configured to acquire electrical signals indicative of heart activity, such as ECG signals and respiratory signals, e.g., impedance signals from variating AC current and DC current signals. Unit 1002 may optionally have at least one sensor port 1020. The ECG of the patient can be sensed as a voltage difference between sensing electrodes 1006.

In some implementations, unit 1002 also includes a measurement circuit 1012 to receive one or more electrical physiological signals of the patient from sensor port 1020. Sensing electrodes 1006 produce heart activity related signals, such as ECG signals and respiratory signals, which are fed into a corresponding cardiac detector and/or respiratory detector of a measuring circuit 1012 to generate ECG and/or respiration data.

Electrical signals in the form of impedance signals may be fed as input to the respiratory detector of the measurement circuit 1012 to determine impedance respiratory data. Impedance can be sensed between electrodes 1006 and/or the connections of sensor port 1020. In implementations, respiratory detector may be configured to render impedance respiratory data of the patient based on received impedance AC signals that can be rendered as a modulation to a carrier signal, as a stream of values, and so on. The measurement circuit 1012 can render or generate health data about the received signals.

Examples of other signal source components 1008 may include sensors or transducers such as a perfusion sensor, a pulse oximeter, a device for detecting blood flow (e.g. a Doppler device), a sensor for detecting blood pressure (e.g. a cuff), an optical sensor, illumination detectors and sensors working together with light sources for detecting color change in tissue, a device that can detect heart wall movement, a sound sensor, a device with a microphone, a Saturation of Peripheral Oxygen ($SpO_2$) sensor, a GPS for example used to determine a sudden cardiac arrest or other cardiac conditions, and so on. Signals from the other signal source components 1008 may be inputted into the measurement circuit 1012, and/or other detector(s) 1018.

The health data is processed by the processor 1030 of the medical monitoring device 1000. In some implementations, processor 1030 may include intelligent hardware, e.g., a central processing unit (CPU), a microcontroller, an application specific integrated circuit (ASIC), etc. The processor 1030 may process instruction for execution within the unit 1002 including instructions stored in memory 1040 or on other data store(s). The processor 1030 may coordinate computing device components, e.g. applications, wireless or wired communication through interfaces, etc. In some implementations, multiple processors and buses may be used.

The processor 1030 may be implemented in a number of ways. Such ways include, by way of example and not limitation, digital and/or analog processors such as microprocessors and Digital Signal Processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on. The processor 1030 may be implemented as a chipset of chips that include separate and multiple analog digital processors. The processor may also be implemented using various architectures. For example, the processor 1030 may be a CISC (Complex Instruction Set Computer) processor, RISC (Reduced Instruction Set Computer) processor or MISC (Minimal Instruction Set Computer) processor, mobile device processors. etc.

Processor 1030 may include, or have access to, a non-transitory storage medium, such as a memory 1040. The memory 1040, which can work together with processor 1030 for storing information and instructions to be executed by the processor. The memory 1040 may also be used for storing temporary variables or other intermediate information during execution of instructions to be executed by the processor.

The "processor" as used herein, includes any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems.

Memory 1040 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. or other tangible media suitable for storing instructions (e.g., program or software instructions) for execution by the processor 1030. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system). Memory 1040 is a non-transitory storage medium.

Memory 1040 can include programs for processor 1030, which processor 1030 may be able to read and execute. More particularly, the programs can include sets of instructions in the form of code, which processor 1030 may be able to execute upon reading. Executing is performed by physical manipulations of physical quantities, and may result in functions, operations, processes, actions and/or methods to be performed, and/or the processor to cause other devices or components or blocks to perform such functions, operations, processes, actions and/or methods. The programs can be operational for the inherent needs of processor 1030, and can also include protocols and ways that decisions can be made.

Memory may be employed to store data, such as health data. This data can include patient data, system data and environmental data, for example as learned by the various source components. The data can be stored in memory 1040 before it is transmitted out of unit 1002, or stored there after it is received by unit 1002.

Processor 1030 can be considered to have a number of modules. In some implementations, and as a matter of convention used herein, instances of the software may be referred to as a "module" and by other similar terms. Generally, a module includes a set of the instructions so as to offer or fulfill a particular functionality. Implementations of modules and the functionality delivered are not limited by the implementations described in this document.

One such module can be a health determination module 1032 to determine a variety of actual or potential health disorders. For example, determination module 1032 may implement logic to an episode of a health event based, at least in part, on the acquired health data.

The processor 1030 can also include additional modules, such as other module 1036, to perform other functions for multiple purposes. For example, the other module 1036 may operate particular source components or other devices. Other modules 1036 may organize the health data in particular ways, such as trend data that may be transferred to data management device(s).

Unit 1002 includes a communication component for establishing one or more wired or wireless communication links with other devices of the medical data management system. The communication component may include various hardware and/or software elements, such as a communication module 1042 and/or user interface 1044.

The communication module 1042 may also include software that enables communications of the user interface 1044 over a network such as the HTTP, TCP/IP, RTP/RTSP, protocols, wireless application protocol (WAP), IEEE 902.11 protocols, and the like. In addition to and/or alternatively, other communications software and transfer protocols may also be used, for example IPX, UDP or the like. The communication network may include a local area network, a wide area network, a wireless network, an Intranet, the Internet, a private network, a public network, a switched network, or any other suitable communication network, such as for example cloud networks. The network may include many interconnected computer systems and any suitable communication links such as hardwire links, optical links, satellite or other wireless communications links such as Bluetooth, Wi-Fi, wave propagation links, or any other suitable mechanisms for communication of information. For example, the network may communicate to one or more mobile wireless devices, such as mobile phones, tablets, and the like, via a base station such as a wireless transceiver.

The network may include one or more of types of communication configurations, such as a gateway, one or more WANs (Wide-Area Networks) and/or LANs (Local-Area Networks), which may be wired and/or wireless. In some examples, the network 140 may include the Internet and/or one or more cellular networks, such as for narrowband data over cellular, among other networks. For example, the network 140 may provide a connection, for example, through a local network to a host computer or to data equipment operated by an Internet Service Provider (ISP). The ISP in turn provides data communication services through the world wide packet data communication network (the "Internet"). For example, the wearable medical device may communicate through one or more gateways to connect with the Internet.

The network may operate according to one or more communication protocols, such as Bluetooth™, Zigbee, Narrowband Internet of Things (NB IoT), LTE (Long-Term Evolution), CDMA (Code Division Multiple Access), WiMax (Worldwide Interoperability for Microwave Access), WiFi (Wireless Fidelity), WiFi Direct (Wireless Fidelity Direct), EDGE (Enhanced Data rates for GSM (Global System Mobile) Evolution), 3G (Third Generation), 4G (Fourth Generation), HTTP (Hyper-Text Transfer Protocol), TCP (Transmission Control Protocol), SIP (Session Initiation Protocol), device contact based transfer protocols, device movement based pairing protocols, and other communication protocols.

User 1046 may include a person and/or computing system. For local interaction with the wearable medical device 1000, the user 1046 may include the patient or a local bystander. In some implementations, the user 1046 may be a remote entity, such as an electronic assistant device of a remote person or a medical server device. For example, the user 1046 may be a health support entity such as a doctor, caregiver, other health care provider, health care service, dispatch, technical service, an authorized person, and so on, including combinations thereof. The user may also include a medical server device or devices such as a cloud service, serving as a repository for health data of the patient.

A user interface 1044 may transmit information to the user 1046 and in some implementations may receive information from the user 1046. The user interface 1044 may be configured to send and receive data and information.

The example wearable medical device 1000 shown is configured to provide cardiac treatments directly to the patient, such as defibrillating the patient, in addition to monitoring health parameters. Defibrillation can be performed by defibrillation components delivering an electrical charge to the body of the patient in the form of an electric shock. The electric shock can be delivered in one or more pulses.

An energy storage module 1052 temporarily stores electrical energy in the form of an electrical charge, when preparing for discharge of a pulse to administer a shock. In implementations, energy storage module 1052 can be charged from a power source 1056 to a designated amount of energy, as controlled by processor 1030. In typical implementations, energy storage module 1052 includes a capacitor 1054, which can be a single capacitor or a system of capacitors, and so on. In some implementations, energy storage module 1052 may include a device that exhibits high power density, such as an ultracapacitor. Capacitor 1054 can store the energy in the form of an electrical charge, for delivering to the patient.

Based on the findings of a cardiac event by the processor 1030, the processor 1030 may further determine that treatment is warranted. In some implementations, the processor 1030 may determine treatment based on additional information as well, such as patient medical history data, event history data, etc. The processor 1030 may initiate a treatment session by treatment initiation module 1034.

Fluid for ejection at the electrodes contact site with the patient may be initially stored in a fluid reservoir (not shown). A fluid deploying mechanism 1074 is configured to cause at least some of the fluid to be released from the reservoir at the initiation of the treatment session, and be deployed near one or both of the patient locations to which the electrodes are configured to be attached. For example a gas deployment mechanism may eject a gas into or adjacent to the fluid reservoir (e.g., gas sack next to a fluid pack) to force the fluid out of the reservoir, through one or more ports in the electrode and onto the body of the patient. In some embodiments, fluid deploying mechanism 1074 is activated responsive to receiving activation signal from processor 1030, prior to the electrical discharge.

The processor 1030 may activate discharge circuit 1070 to deliver an appropriate shock treatment to the patient. In some implementations, when the determination is to shock, an electrical charge pulse is delivered to the patient. Delivering the electrical charge is also known as discharging. Shocking can be for defibrillation, pacing, and so on.

Defibrillation port 1058 includes electrical nodes 1060, 1062. Leads of defibrillation electrodes 1064, 1066 can be plugged into defibrillation port 1058, so as to make electrical contact with nodes 1060, 1062, respectively. It is also possible that defibrillation electrodes 1064, 1066 are connected continuously to defibrillation port 1058, instead. Either way, defibrillation port 1058 can be used for guiding, via electrodes, the electrical charge that has been stored in an energy storage module 1052, to the patient.

Discharge circuit 1070 can include one or more switches 1072, which may also include one or more bridges. Switches 1072 can be made in a number of ways, such as by an H-bridge, cross-bar switch, or other switching mechanisms to control current flow. Discharge circuit 1072 can also be controlled by a user or external computing device via user interface 1044. Measuring circuit 1012 can further monitor the amount of electrical current provided from the discharge circuit 1072 prior to release to the patient.

When the defibrillation electrodes 1064, 1066 make sufficient electrical contact with the body of the patient, the unit 1002 can administer, via the defibrillation electrodes 1064, 1066, a brief, strong electric pulse through the body. The pulse is also known as defibrillation pulse, shock, defibrillation shock, therapy, electrotherapy, therapy shock, etc. The pulse is intended to go through and restart the heart, in an effort to save the life of the patient. The defibrillation pulse can have an energy suitable for its purpose, such as at least 100 Joule ("J"), 200 J, 300 J, and so on.

In some implementations, defibrillation electrodes 1064, 1066 may be multi-functional to also provide electrical signals to measurement circuit 1012 to generate ECG data and/or respiratory data. In such implementations, the medical monitoring device system 1000 may include both defibrillation electrodes 1064, 1066 and sensing electrodes 1006, or may include the multi-functional defibrillation electrodes 1064, 1066 without also dedicated sensing electrodes 1006.

In some implementations, cardiac treatment may include providing a pacing pulses with energies similar to pacers rather than defibrillators, if processor 1030 determines that pacing is appropriate according to the health data. For pacer implementations, at least some of the stored electrical charge can be caused to be discharged via at least two of the defibrillation electrodes 1064, 1066 through the patient, so as to deliver to the patient a pacing sequence of pacing pulses. The pacing pulses may be periodic, and thus define a pacing period and the pacing rate. There is no requirement, however, that the pacing pulses be exactly periodic. A pacing pulse can have an energy suitable for its purpose, such as at most 100 J, 25 J, usually about 10 J, and so on. In either case, the pulse has a waveform suitable for this purpose.

When the decision of the detection module 1032 is to provide electrical discharge in the form of a pace, i.e., to deliver pacing pulses, the processor 1030 can be configured to cause control the discharge circuit 1070 to discharge through the patient at least some of the electrical charge provided by the power source 1056. Since pacing requires lesser charge and/or energy than a defibrillation shock, in some implementations, pacing wiring 1074 is provided from the power source 1056 to the discharge circuit 1070.

Any suitable programming languages and programming techniques may be used to implement the routines of particular embodiments. Different programming techniques may be employed such as procedural or object-oriented. The routines may be executed on a single processing device or multiple processors. Although the steps, operations, or computations may be presented in a specific order, the order may be changed in different particular embodiments. In some particular embodiments, multiple steps shown as sequential in this specification may be performed at the same time. A number of implementations have been described. Features described with conditional language may describe implementations that are optional. The functional blocks, methods, devices, and systems described in the present disclosure may be integrated or divided into different combinations of systems, devices, and functional blocks as would be known to those skilled in the art.

The devices and/or systems described in this document perform functions, processes and/or methods. These functions, processes and/or methods may be implemented by one or more devices that include logic circuitry. Such a device can be alternately called a computer, and so on. It may be a standalone device or computer, such as a general purpose computer, or part of a device that has one or more additional functions. The logic circuitry may include a processor and non-transitory computer-readable storage media, such as memories, of the type described elsewhere in this document. Often, for the sake of convenience only, it is preferred to implement and describe a program as various interconnected distinct software modules or features. These, along with data are individually and also collectively known as software. In some instances, software is combined with hardware, in a mix called firmware.

This detailed description includes flowcharts, display images, algorithms, and symbolic representations of program operations that may be provided within at least one non-transitory, tangible, computer readable medium for execution by the one or more processors. An economy is achieved in that flowchart, as in FIG. 8 is used to describe both programs, and also methods. So, while flowcharts described methods in terms of boxes, they also can concurrently describe programs to direct the processes described.

Other implementations include combinations and sub-combinations of features described or shown in the drawings herein, including for example, implementations that are equivalent to: providing or applying a feature in a different order than in a described implementation, extracting an individual feature from one and inserting such feature into another implementations; removing one or more features from an implementation; or both removing one or more features from an implementation and adding one or more features extracted from one or more other implementations, while providing the advantages of the features incorporated in such combinations and sub-combinations. As used in this paragraph, feature or features can refer to the structures and/or functions of an apparatus, article of manufacture or system, and/or the steps, acts, or modalities of a method.

We claim:

1. A wearable medical device for cardiac defibrillation of a patient, the wearable medical device comprising:
- a defibrillator electrode pad for providing electrical shock treatment to the patient upon activation;
- a wearable article comprising:
  - one or more flexible support material configured to hold a containment portion on the patient, the containment portion being sized to house the defibrillator electrode pad and the containment portion comprising a spacer structure positioned to provide a cushioned area for resisting pressure build-up within the containment portion and enable distribution of pressure exerted across the defibrillator electrode pad during the electrical shock treatment, the spacer structure comprising:
  - a top permeable layer positioned toward the defibrillator electrode pad;
  - a bottom permeable layer opposite of the top permeable layer; and a compressible middle layer having a plurality of springy elements dispersed between the top permeable layer and the bottom permeable layer for airflow through the spacer structure and the springy elements being attached to the top permeable layer at one end and bottom permeable layer at another end, enabling compression of the middle layer during the pressure build-up; and one or more processors to determine the electrical shock treatment and based on the determination, to activate the defibrillator electrode pad.

2. The wearable medical device of claim 1, wherein the top permeable layer and/or the bottom permeable layer include a knitted mesh and the plurality of springy elements include a plurality of knitted filaments.

3. The wearable medical device of claim 1, wherein the containment portion further comprises:

one or more fluid packs coupled to the defibrillator electrode pad to release fluid upon injection of a gas into the containment portion; and an outer layer coupled with the spacer structure.

4. The wearable medical device of claim 3, wherein the outer layer is a stiffened material having a greater rigidity than a rigidity of the one or more flexible support material.

5. The wearable medical device of claim 1, wherein the containment portion further comprises an electrically conducting lining configured to contact the defibrillator electrode pad proximal to the patient.

6. The wearable medical device of claim 1, further comprising one or more monitoring electrodes to detect electrical signals for generating electrocardiogram (ECG) data, wherein the one or more processors determine the electrical shock treatment based, at least in part, on the ECG data.

7. The wearable medical device of claim 1, wherein the containment portion further comprises an electrically conducting lining configured to contact the defibrillator electrode pad proximal to the patient.

8. The wearable medical device of claim 1, further comprising one or more monitoring electrodes to detect electrical signals for generating electrocardiogram (ECG) data, wherein the one or more processors determine the electrical shock treatment based, at least in part, on the ECG data.

9. A method of providing cardiac defibrillation to a patient using a wearable article of a medical device, the method comprising:

inserting a defibrillator electrode pad into a containment portion of a wearable article, the containment portion comprising: an attached spacer structure positioned to provide a cushioned area for pressure on the defibrillator electrode pad, one or more fluid packs coupled to the defibrillator electrode pad, and an outer layer coupled with the spacer structure, the spacer structure comprising:

a top permeable layer positioned toward the defibrillator electrode pad;

a bottom permeable layer opposite of the top permeable layer; and a compressible middle layer having a plurality of springy elements dispersed between the top permeable layer and the bottom permeable layer for airflow through the spacer structure;

activating a treatment session for the patient;

in response to activating the treatment session, injecting a gas into or adjacent to the one or more fluid packs, thereby causing the spacer structure to compress and change shape in resistance to a pressure increase within the containment portion, enabling fluid to be released from the one or more fluid packs at the defibrillator electrode pad onto the patient, and enabling the pressure to be exerted onto the defibrillator electrode pad in a direction toward the patient; and activating the defibrillator electrode pad to provide an electrical shock treatment to the patient by one or more electrodes.

10. The method of claim 9, wherein activating the treatment session is in response, at least in part, to ECG data generated according to electrical signals detected by one or more monitoring electrodes of the medical device.

11. The method of claim 10, wherein the one or more electrodes include the one or more monitoring electrodes to detect the electrical signals and further serve to provide the electrical shock treatment.

12. The method of claim 9, wherein upon completion of the electrical shock treatment, the method further comprises:

removing the electrode pad from the containment portion; and washing the wearable article with the attached spacer structure, for future use by the patient.

13. The method of claim 9, wherein the top permeable layer and/or the bottom permeable layer include a knitted mesh and the plurality of springy elements include a plurality of knitted filaments extending between the top permeable layer and the bottom permeable layer.

14. A wearable medical device for cardiac defibrillation of a patient, the wearable medical device comprising:

a defibrillator electrode pad for providing electrical shock treatment to the patient upon activation;

a wearable article comprising:

one or more flexible support material configured to hold a containment portion on the patient, the containment portion being sized to house the defibrillator electrode pad, and the containment portion comprising:

one or more fluid packs coupled to the defibrillator electrode pad to release fluid upon injection of a gas into the containment portion;

a spacer structure positioned to provide a cushioned area for pressure on the defibrillator electrode pad during the electrical shock treatment; and an outer layer coupled with the spacer structure, the spacer structure comprising:

a top permeable layer positioned toward the defibrillator electrode pad;

a bottom permeable layer opposite of the top permeable layer; and a compressible middle layer having a plurality of springy elements dispersed between the top permeable layer and the bottom permeable layer for airflow through the spacer structure, wherein the spacer structure is configured to resist pressure increase in the containment portion, thereby enabling pressure to be exerted onto the defibrillator electrode pad in a direction toward the patient; and one or more processors to determine the electrical shock treatment and based on the determination, to activate the defibrillator electrode pad.

15. The wearable medical device of claim 14, wherein the top permeable layer and/or the bottom permeable layer include a knitted mesh and the plurality of springy elements include a plurality of knitted filaments extending between the top permeable layer and the bottom permeable layer.

16. The wearable medical device of claim 14, wherein the outer layer is a stiffened material having a greater rigidity than a rigidity of the one or more flexible support material.

* * * * *